(12) United States Patent
Hida et al.

(10) Patent No.: US 10,160,734 B2
(45) Date of Patent: *Dec. 25, 2018

(54) DICHROIC DYE COMPOUND, POLARIZING FILM, AND USES THEREOF

(71) Applicant: Sumitomo Chemical Company, Limited, Tokyo (JP)

(72) Inventors: Noriyuki Hida, Osaka (JP); Haruki Okawa, Niihama (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 15/519,250

(22) PCT Filed: Oct. 14, 2015

(86) PCT No.: PCT/JP2015/079071
§ 371 (c)(1),
(2) Date: Apr. 14, 2017

(87) PCT Pub. No.: WO2016/060172
PCT Pub. Date: Apr. 21, 2016

(65) Prior Publication Data
US 2017/0226071 A1    Aug. 10, 2017

(30) Foreign Application Priority Data

Oct. 17, 2014 (JP) ................................. 2014-212368
Jun. 3, 2015 (JP) ................................. 2015-112873

(51) Int. Cl.
| | | |
|---|---|---|
| *C07D 277/60* | (2006.01) |
| *C08K 5/23* | (2006.01) |
| *C08K 5/372* | (2006.01) |
| *C07D 417/02* | (2006.01) |
| *C08K 5/55* | (2006.01) |
| *C08K 5/04* | (2006.01) |
| *C07C 22/08* | (2006.01) |
| *G02F 1/13* | (2006.01) |

(52) U.S. Cl.
CPC ............ *C07D 277/60* (2013.01); *C07C 22/08* (2013.01); *C07D 417/02* (2013.01); *C08K 5/04* (2013.01); *C08K 5/23* (2013.01); *C08K 5/3725* (2013.01); *C08K 5/55* (2013.01); *G02F 1/13* (2013.01)

(58) Field of Classification Search
CPC ...... C07D 277/60; C07D 417/02; C08K 5/23; C08K 5/3725; C08K 5/55; C08K 5/04; C07C 22/08; G02F 1/13
USPC ....................................................... 524/560
See application file for complete search history.

(56) References Cited

U.S. PATENT DOCUMENTS

| | | |
|---|---|---|
| 4,959,172 A | 9/1990 | Miura et al. |
| 7,750,130 B2 | 7/2010 | Han et al. |
| 7,763,330 B2 | 7/2010 | Lub et al. |
| 2007/0264213 A1* | 11/2007 | Han .................... C09B 29/0003 424/63 |
| 2010/0051871 A1 | 3/2010 | Han et al. |
| 2015/0337203 A1 | 11/2015 | Hida et al. |

FOREIGN PATENT DOCUMENTS

| | | |
|---|---|---|
| CN | 103333083 A | 10/2013 |
| CN | 103360787 A | 10/2013 |
| JP | S56104984 A | 8/1981 |

(Continued)

OTHER PUBLICATIONS

Brode et al., J. Am. Chem. Soc., 74, 4641-4646, 1952.*

(Continued)

*Primary Examiner* — Hui H Chin
(74) *Attorney, Agent, or Firm* — Panitch Schwarze Belisario & Nadel LLP

(57) ABSTRACT

A compound having a maximum absorption in a wavelength range of 350 nm to 550 nm that functions as a dichroic dye is provided. In particular, a compound represented by formula (1) is provided. In the compound of formula (1), $R^1$ represents an alkyl group having 1 to 20 carbon atoms or the like; $R^2$ represents an acyl group having 1 to 20 carbon atoms or the like; $R^3$ represents a hydrogen atom or the like; and Y represents a group of formula (Y1). In the formula (Y1), * represents a bonding site with N, or a group of formula (Y2). In the formula (Y2), * represents a bonding site with N; $P^1$ and $P^2$ each independently represent —S— or the like; and $Q^1$ and $Q^2$ each independently represent =N— or the like.

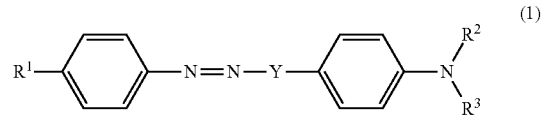

(1)

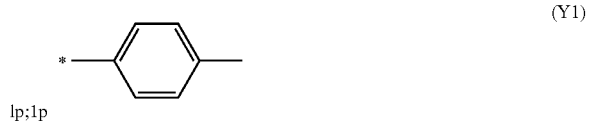

(Y1)

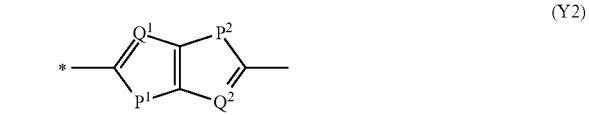

(Y2)

16 Claims, 2 Drawing Sheets

(56) References Cited

FOREIGN PATENT DOCUMENTS

| | | | |
|---|---|---|---|
| JP | S560104984 A | 8/1981 | |
| JP | S58038756 A | 3/1983 | |
| JP | 2000313881 A | 11/2000 | |
| JP | 2007510946 A | 4/2007 | |
| JP | 2007-326846 A | 12/2007 | |
| JP | 2016006502 A | 1/2016 | |

OTHER PUBLICATIONS

Brode et al., J. Am. Chem. Soc., 63, 1502-1505, 1941.*
Int'l Preliminary Report on Patentability dated Jan. 19, 2016 in Int'l Application No. PCT/JP2015/079071.
Office Action dated Jul. 4, 2018 in CN Application No. 201580055924.4.

* cited by examiner

DICHROIC DYE COMPOUND, POLARIZING FILM, AND USES THEREOF

CROSS-REFERENCE TO RELATED APPLICATION

This application is a Section 371 of International Application No. PCT/JP2015/079071, filed Oct. 14, 2015, which was published in the Japanese language on Apr. 21, 2016 under International Publication No. WO 2016/060172 A1, and the disclosure of which is incorporated herein by reference.

TECHNICAL FIELD

The present invention relates to a compound and a composition.

BACKGROUND ART

Patent Document 1 describes a polarizing film including a dichroic dye dispersed in an orientated polymerizable liquid crystal compound.

Patent Document 2 describes, as a dichroic dye having a maximum absorption in a wavelength range of 350 nm to 550 nm, a bisazo dye having a 1,4-naphthyl structure. However, a dichroic ratio of a polarizing film including the dichroic dye has been low.

PRIOR ART DOCUMENT

Patent Documents

Patent Document 1: JP-T-2007-510946
Patent Document 2: JP 1454637 (JP-B-S63-1357)

SUMMARY OF THE INVENTION

Problem to be Solved by the Invention

There has been required a compound having a maximum absorption in a wavelength range of 350 nm to 550 nm and functioning as a dichroic dye.

Means for Solving the Problem

The present invention includes the followings.
[1] A compound represented by formula (1):

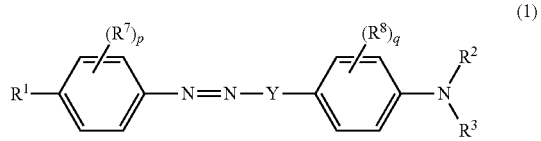

(1)

wherein $R^1$ represents an alkyl group having 1 to 20 carbon atoms, an alkoxy group having 1 to 20 carbon atoms, an acyl group having 1 to 20 carbon atoms, an alkoxycarbonyl group having 2 to 20 carbon atoms, an acyloxy group having 1 to 20 carbon atoms, or —N($R^{10}$)($R^{11}$), wherein $R^{10}$ represents an acyl group having 1 to 20 carbon atoms, an alkylsulfonyl group having 1 to 20 carbon atoms, or an arylsulfonyl group having 6 to 20 carbon atoms, $R^{11}$ represents a hydrogen atom or an alkyl group having 1 to 20 carbon atoms, $R^{10}$ and $R^{11}$ may be joined together to form a ring containing —N—CO— or —N—SO$_2$— together with the nitrogen atom to which they are bonded, at least one hydrogen atom constituting the alkyl group, the alkoxy group, the acyl group, the alkoxycarbonyl group, the acyloxy group, the alkylsulfonyl group, and the arylsulfonyl group may be replaced by a halogen atom, a hydroxy group, an amino group, or an amino group having a substituent, —O— or —NR$^{20}$— may be inserted between carbon atoms constituting the alkyl group and the alkoxy group, wherein $R^{20}$ represents a hydrogen atom or an alkyl group having 1 to 20 carbon atoms;

$R^7$ and $R^8$ are substituents other than a hydrogen atom, each independently represent an alkyl group having 1 to 4 carbon atoms, an alkoxy group having 1 to 4 carbon atoms, a halogen atom, or a cyano group, at least one hydrogen atom constituting the alkyl group having 1 to 4 carbon atoms and the alkoxy group having 1 to 4 carbon atoms may be substituted with a halogen atom or a hydroxy group, p and q are each independently an integer from 0 to 2;

$R^2$ represents an acyl group having 1 to 20 carbon atoms, an alkylsulfonyl group having 1 to 20 carbon atoms, or an arylsulfonyl group having 6 to 20 carbon atoms; $R^3$ represents a hydrogen atom or an alkyl group having 1 to 20 carbon atoms, $R^2$ and $R^3$ may be joined together to form a ring containing —N—CO— or —N—SO$_2$— together with the nitrogen atom to which they are bonded, at least one hydrogen atom constituting the acyl group, the alkylsulfonyl group, and the arylsulfonyl group may be replaced by a halogen atom, a hydroxy group, an amino group, or an amino group having a substituent, —O— or —NR$^{21}$— may be inserted between carbon atoms constituting the alkyl group and the alkoxy group, wherein $R^{21}$ represents a hydrogen atom or an alkyl group having 1 to 20 carbon atoms; and Y represents a group of formula (Y1):

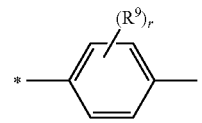

(Y1)

wherein * represents a bonding site with N; $R^9$ is a substituent other than a hydrogen atom, independently represents an alkyl group having 1 to 4 carbon atoms, an alkoxy group having 1 to 4 carbon atoms, a halogen atom, or a cyano group, at least one hydrogen atom constituting the alkyl group having 1 to 4 carbon atoms and the alkoxy group having 1 to 4 carbon atoms may be substituted with a halogen atom or a hydroxy group; r is an integer from 0 to 2, or a group of formula (Y2):

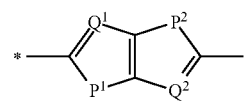

(Y2)

wherein * represents a bonding site with N; $P^1$ and $P^2$ each independently represent —S—, —O—, or —N($R^{12}$)—, wherein $R^{12}$ represents a hydrogen atom or an alkyl group having 1 to 4 carbon atoms; and $Q^1$ and $Q^2$ each independently represent =N— or =CH—.

[2] The compound according to [1], wherein p, q, and r are 0.
[3] A composition comprising a polymerizable liquid crystal compound and the compound according to [1] or [2].
[4] The composition according to [3], wherein the polymerizable liquid crystal compound exhibits a smectic liquid crystal phase.
[5] The composition according to [3] or [4], further comprising a polymerization initiator.
[6] A polarizing film comprising the compound according to [1] or [2].
[7] A polarizing film formed of the composition according to any one of [3] to [5].
[8] The polarizing film according to [6] or [7], wherein a maximum absorption wavelength ($\lambda_{max1}$) of the polarizing film is longer than a maximum absorption wavelength ($\lambda_{max2}$) of the compound represented by formula (1).
[9] The polarizing film according to [8], wherein a difference between $\lambda_{max1}$ and $\lambda_{max2}$ is not less than 15 nm.
[10] The polarizing film according to any one of [6] to [9], wherein a Bragg peak is exhibited in X-ray diffractometry.
[11] A liquid crystal display device comprising the polarizing film according to any one of [6] to [10].
[12] A liquid crystal cell comprising the polarizing film according to any one of [6] to [10], a liquid crystal layer, and a base.
[13] The liquid crystal cell according to [12], wherein the polarizing film is disposed between the base and the liquid crystal layer.
[14] The liquid crystal cell according to [13], wherein a color filter is further disposed between the base and the liquid crystal layer.
[15] A circularly polarizing plate comprising the polarizing film according to any one of [6] to [10] and a ¼ wavelength plate.
[16] An organic EL display device comprising the polarizing film according to any one of [6] to [10] and an organic EL element.
[17] An organic EL display device comprising the circularly polarizing plate according to [15] and an organic EL element.
[18] A method for producing a compound represented by formula (1):

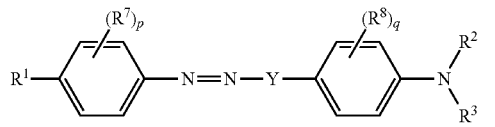

(1)

wherein $R^1$ represents an alkyl group having 1 to 20 carbon atoms, an alkoxy group having 1 to 20 carbon atoms, an acyl group having 1 to 20 carbon atoms, an alkoxycarbonyl group having 2 to 20 carbon atoms, an acyloxy group having 1 to 20 carbon atoms, or —N($R^{10}$)($R^{11}$), wherein $R^{10}$ represents an acyl group having 1 to 20 carbon atoms, an alkylsulfonyl group having 1 to 20 carbon atoms, or an arylsulfonyl group having 6 to 20 carbon atoms, $R^{11}$ represents a hydrogen atom or an alkyl group having 1 to 20 carbon atoms, $R^{10}$ and $R^{11}$ may be joined together to form a ring containing —N—CO— or —N—SO$_2$— together with the nitrogen atom to which they are bonded, at least one hydrogen atom constituting the alkyl group, the alkoxy group, the acyl group, the alkoxycarbonyl group, the acyloxy group, the alkylsulfonyl group, and the arylsulfonyl group may be replaced by a halogen atom, a hydroxy group, an amino group, or an amino group having a substituent, —O— or —NR$^{20}$— may be inserted between carbon atoms constituting the alkyl group and the alkoxy group, wherein $R^{20}$ represents a hydrogen atom or an alkyl group having 1 to 20 carbon atoms;

$R^2$ represents an acyl group having 1 to 20 carbon atoms, an alkylsulfonyl group having 1 to 20 carbon atoms, or an arylsulfonyl group having 6 to 20 carbon atoms; $R^3$ represents a hydrogen atom or an alkyl group having 1 to 20 carbon atoms, $R^2$ and $R^3$ may be joined together to form a ring containing —N—CO— or —N—SO$_2$— together with the nitrogen atom to which they are bonded, at least one hydrogen atom constituting the acyl group, the alkylsulfonyl group, and the arylsulfonyl group may be replaced by a halogen atom, a hydroxy group, an amino group, or an amino group having a substituent, —O— or —NR$^{21}$— may be inserted between carbon atoms constituting the alkyl group and the alkoxy group, wherein $R^{21}$ represents a hydrogen atom or an alkyl group having 1 to 20 carbon atoms;

$R^7$ is a substituent other than a hydrogen atom, independently represents an alkyl group having 1 to 4 carbon atoms, an alkoxy group having 1 to 4 carbon atoms, a halogen atom, or a cyano group, at least one hydrogen atom constituting the alkyl group having 1 to 4 carbon atoms and the alkoxy group having 1 to 4 carbon atoms may be substituted with a halogen atom or a hydroxy group, p is an integer from 0 to 2;

$R^8$ is a substituent other than a hydrogen atom, independently represents an alkyl group having 1 to 4 carbon atoms, an alkoxy group having 1 to 4 carbon atoms, a halogen atom, or a cyano group, at least one hydrogen atom constituting the alkyl group having 1 to 4 carbon atoms and the alkoxy group having 1 to 4 carbon atoms may be substituted with a halogen atom or a hydroxy group, q is an integer from 0 to 2; and Y represents a group of formula (Y1):

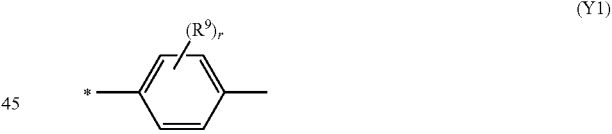

(Y1)

wherein * represents a bonding site with N; $R^9$ represents an alkoxy group having 1 to 4 carbon atoms, a halogen atom, or a cyano group, at least one hydrogen atom constituting the alkyl group having 1 to 4 carbon atoms and the alkoxy group having 1 to 4 carbon atoms may be substituted with a halogen atom or a hydroxy group; r is an integer from 0 to 2, or a group of formula (Y2):

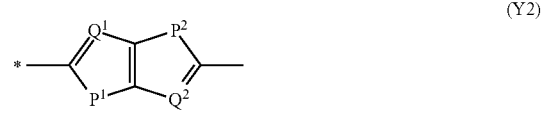

(Y2)

wherein * represents a bonding site with N; $P^1$ and $P^2$ each independently represent —S—, —O—, or —N($R^{12}$)—, wherein $R^{12}$ represents a hydrogen atom or an alkyl group having 1 to 4 carbon atoms; $Q^1$ and $Q^2$ each independently represent =N— or =CH—, the method comprising reacting a compound represented by formula (2):

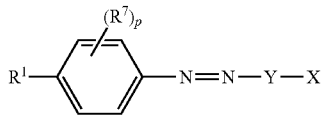
(2)

wherein X represents a chlorine atom, a bromine atom, or an iodine atom; and $R^1$, $R^7$, and Y are respectively the same meaning as above,
with a compound represented by formula (3):

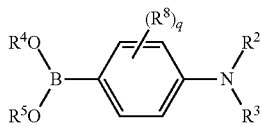
(3)

wherein $R^2$, $R^3$, and $R^8$ are respectively the same meaning as above; and $R^4$ and $R^5$ each independently represent a hydrogen atom or an alkyl group having 1 to 10 carbon atoms, $R^4$ and $R^5$ may be joined together to form a ring containing —O—B—O— together with the oxygen atom and the boron atom to which they are bonded.

Effect of the Invention

The compound of the present invention is a novel compound having a maximum absorption in a wavelength range of 350 nm to 550 nm and functioning as a dichroic dye, and a polarizing film having a high dichroic ratio can be formed of a composition containing the compound.

MODE FOR CARRYING OUT THE INVENTION

Figure 1:
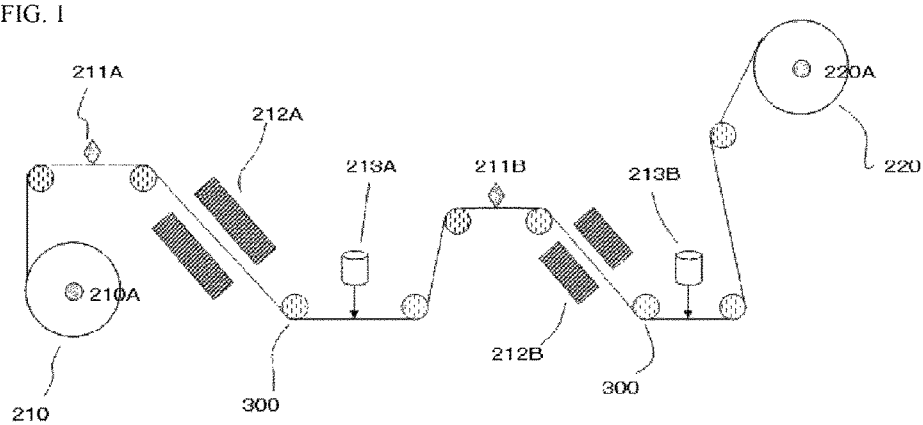
FIG. 1 is schematic diagram showing a process for continuously producing a polarizing film of the present invention.

<Compound Represented by Formula (1)>
An azo group of the present compound represented by formula (1) (hereinafter, may also be referred to as compound (1)) is preferably a trans-type azo group.
In formula (1), $R^1$ represents an alkyl group having 1 to 20 carbon atoms, an alkoxy group having 1 to 20 carbon atoms, an acyl group having 1 to 20 carbon atoms, an alkoxycarbonyl group having 2 to 20 carbon atoms, an acyloxy group having 1 to 20 carbon atoms, or —N($R^{10}$)($R^{11}$).

Examples of the alkyl group having 1 to 20 carbon atoms include unsubstituted (no substituent) linear or branched alkyl groups having 1 to 20 carbon atoms, such as a methyl group, an ethyl group, a n-propyl group, an isopropyl group, a n-butyl group, an isobutyl group, a tert-butyl group, a n-pentyl group, an isopentyl group, a neopentyl group, a n-hexyl group, a n-heptyl group, a n-octyl group, a n-nonyl group, and a n-decyl group.

At least one hydrogen atom constituting the alkyl group having 1 to 20 carbon atoms may be substituted with a halogen atom (such as a fluorine atom), a hydroxy group, an amino group, or an amino group having a substituent. Examples of the amino group having a substituent include amino groups substituted with one or two alkyl groups having 1 to 20 carbon atoms, such as an N-methylamino group, an N-ethylamino group, an N,N-dimethylamino group, and an N,N-diethylamino group. Examples of an alkyl group in which at least one hydrogen atom has been replaced by a halogen atom or the like include haloalkyl groups having 1 to 20 carbon atoms, such as a fluoromethyl group, a trifluoromethyl group, a pentafluoroethyl group, and a nonafluorobutyl group; hydroxyalkyl groups having 1 to 20 carbon atoms, such as a hydroxymethyl group and a 2-hydroxyethyl group; and alkyl groups having 1 to 20 carbon atoms and having an amino group with no substituent or a substituent, such as an aminomethyl group and a 2-(N,N-dimethylamino)ethyl group.

—O— or —$NR^{20}$— may be inserted between carbon atoms constituting the alkyl group, $R^{20}$ represents a hydrogen atom or an alkyl group having 1 to 20 carbon atoms, and examples of the alkyl group having 1 to 20 carbon atoms include the same groups as those described above. Examples of an alkyl group in which —O— or —$NR^{20}$— is inserted between carbon atoms include a methoxymethyl group, a 2-ethoxyethyl group, a 2-(2-ethoxyethoxy)ethyl group, and 2-[2-(ethylamino)ethyl)amino]ethyl group.

Examples of the alkoxy group having 1 to 20 carbon atoms include unsubstituted, linear or branched alkoxy groups having 1 to 20 carbon atoms, such as a methoxy group, an ethoxy group, a n-propoxy group, an isopropoxy group, a n-butoxy group, an isobutoxy group, a tert-butoxy group, a n-pentyloxy group, an isopentyloxy group, a neopentyloxy group, a n-hexyloxy group, a n-heptyloxy group, a n-octyloxy group, a n-nonyloxy group, and a n-decyloxy group.

At least one hydrogen atom constituting the alkoxy group having 1 to 20 carbon atoms may be substituted with a halogen atom (such as a fluorine atom), a hydroxy group, an amino group, or an amino group having a substituent. Examples of the amino group having a substituent include amino groups substituted with one or two alkyl groups having 1 to 20 carbon atoms, such as an N-methylamino group, an N-ethylamino group, an N,N-dimethylamino group, and an N,N-diethylamino group. Examples of an alkoxy group in which at least one hydrogen atom has been replaced by a halogen atom or the like include haloalkoxy groups having 1 to 20 carbon atoms, such as a fluoromethoxy group, a trifluoromethoxy group, a pentafluoroethoxy group, and a nonafluorobutoxy group; hydroxyalkoxy groups having 1 to 20 carbon atoms, such as a hydroxymethoxy group and a 2-hydroxyethoxy group; and alkoxy groups having 1 to 20 carbon atoms and having an amino group with no substituent or a substituent, such as an aminomethoxy group and a 2-(N,N-dimethylamino)ethoxy group.

—O— or —$NR^{20}$— may be inserted between carbon atoms constituting the alkoxy group, and examples of an alkoxy group in which —O— or —NR$^{20}$— is inserted between carbon atoms include a methoxymethoxy group, a 2-ethoxyethoxy group, a 2-(2-ethoxyethoxy)ethoxy group, and a 2-[2-[(ethylamino)ethyl)amino]ethoxy group.

Examples of the acyl group having 1 to 20 carbon atoms include unsubstituted acyl groups having 1 to 20 carbon atoms, such as a formyl group, an acetyl group, an ethylcarbonyl group, a n-propylcarbonyl group, an isopropylcarbonyl group, a n-butylcarbonyl group, an isobutylcarbonyl group, a tert-butylcarbonyl group, a n-pentylcarbonyl group, an isopentylcarbonyl group, a neopentylcarbonyl group, a n-hexylcarbonyl group, a n-heptylcarbonyl group, a n-octylcarbonyl group, a n-nonylcarbonyl group, and a n-decylcarbonyl group. At least one hydrogen atom constituting the acyl group may be substituted with a halogen atom (such as a fluorine atom), a hydroxy group, an amino group, or an amino group having a substituent. Examples of the amino group having a substituent include amino groups substituted with one or two alkyl groups having 1 to 20 carbon atoms, such as an N-methylamino group, an N-ethylamino group, an N,N-dimethylamino group, and an N,N-diethylamino group. Examples of an acyl group in which at least one hydrogen atom has been replaced by a halogen atom or the like include haloacyl groups having 1 to 20 carbon atoms, such as a trifluoroacetyl group, a pentafluoroethylcarbonyl group, and a nonafluorobutylcarbonyl group.

Examples of the alkoxycarbonyl group having 2 to 20 carbon atoms include unsubstituted alkoxycarbonyl groups having 2 to 20 carbon atoms, such as a methoxycarbonyl group, an ethoxycarbonyl group, a n-propoxycarbonyl group, an isopropoxycarbonyl group, a n-butoxycarbonyl group, an isobutoxycarbonyl group, a tert-butoxycarbonyl group, a n-pentyloxycarbonyl group, an isopentyloxycarbonyl group, a neopentyloxycarbonyl group, a n-hexyloxycarbonyl group, a n-heptyloxycarbonyl group, a n-octyloxycarbonyl group, a n-nonyloxycarbonyl group, and a n-decyloxycarbonyl group. At least one hydrogen atom constituting the alkoxycarbonyl group may be substituted with a halogen atom (such as a fluorine atom), a hydroxy group, an amino group, or an amino group having a substituent. Examples of the amino group having a substituent include amino groups substituted with one or two alkyl groups having 1 to 20 carbon atoms, such as an N-methylamino group, an N-ethylamino group, an N,N-dimethylamino group, and an N,N-diethylamino group. Examples of an alkoxycarbonyl group in which at least one hydrogen atom has been replaced by a halogen atom or the like include haloalkoxycarbonyl groups having 2 to 20 carbon atoms, such as a fluoromethoxycarbonyl group, a trifluoromethoxycarbonyl group, a pentafluoroethoxycarbonyl group, and a nonafluorobutoxycarbonyl group.

Examples of the acyloxy group having 1 to 20 carbon atoms include unsubstituted acyloxy groups having 1 to 20 carbon atoms, such as an acetyloxy group, an ethylcarbonyloxy group, a n-propylcarbonyloxy group, an isopropylcarbonyloxy group, a n-butylcarbonyloxy group, an isobutylcarbonyloxy group, a tert-butylcarbonyloxy group, a n-pentylcarbonyloxy group, an isopentylcarbonyloxy group, a neopentylcarbonyloxy group, a n-hexylcarbonyloxy group, a n-heptylcarbonyloxy group, a n-octylcarbonyloxy group, a n-nonylcarbonyloxy group, and a n-decylcarbonyloxy group. At least one hydrogen atom constituting the acyloxy group may be substituted with a halogen atom (such as a fluorine atom), a hydroxy group, an amino group, or an amino group having a substituent. Examples of the amino group having a substituent include amino groups substituted with one or two alkyl groups having 1 to 20 carbon atoms, such as an N-methylamino group, an N-ethylamino group, an N,N-dimethylamino group, and an N,N-diethylamino group. Examples of an acyloxy group in which at least one hydrogen atom has been replaced by a halogen atom or the like include haloacyloxy groups having 1 to 20 carbon atoms, such as a fluoroacetyloxy group, a trifluoroacetyloxy group, a pentafluoroethylcarbonyloxy group, and a nonafluorobutylcarbonyloxy group.

In —N($R^{10}$)($R^{11}$), $R^{10}$ represents an acyl group having 1 to 20 carbon atoms, an alkylsulfonyl group having 1 to 20 carbon atoms, or an arylsulfonyl group having 6 to 20 carbon atoms, $R^{11}$ represents a hydrogen atom or an alkyl group having 1 to 20 carbon atoms, $R^{10}$ and $R^{11}$ may be joined together to form a ring containing —N—CO— or —N—SO$_2$— together with the nitrogen atom to which they are bonded. At least one hydrogen atom constituting the acyl group, the alkylsulfonyl group, and the arylsulfonyl group in $R^{10}$ may be substituted with a halogen atom (such as a fluorine atom), a hydroxy group, an amino group, or an amino group having a substituent. Examples of the amino group having a substituent include amino groups substituted with one or two alkyl groups having 1 to 20 carbon atoms, such as an N-methylamino group, an N-ethylamino group, an N,N-dimethylamino group, and an N,N-diethylamino group. —O— or —NR$^{20}$— may be inserted between carbon atoms constituting the alkyl group in $R^{11}$. Examples of the acyl group having 1 to 20 carbon atoms in $R^{10}$ include the same groups as those for the acyl groups having 1 to 20 carbon atoms in $R^1$. Examples of an acyl group in which at least one hydrogen atom constituting the acyl group has been replaced by a halogen atom or the like include the same groups as those for the acyl groups in $R^1$.

Examples of the alkylsulfonyl group having 1 to 20 carbon atoms include unsubstituted alkylsulfonyl groups having 1 to 20 carbon atoms, such as a methylsulfonyl group, an ethylsulfonyl group, and a n-propylsulfonyl group. Examples of a group in which at least one hydrogen atom constituting the alkylsulfonyl group has been replaced by a halogen atom or the like include haloalkylsulfonyl groups having 1 to 20 carbon atoms, such as a trifluoromethylsulfonyl group, a pentafluoroethylsulfonyl group, a pentafluoro-n-propylsulfonyl group.

Examples of the arylsulfonyl group having 6 to 20 carbon atoms include a benzenesulfonyl group and a p-toluenesulfonyl group. Examples of a group in which at least one hydrogen atom constituting the arylsulfonyl group has been replaced by a halogen atom or the like include a p-trifluoromethylbenzenesulfonyl group.

Examples of the alkyl group having 1 to 20 carbon atoms in $R^{11}$ include the same groups as those for the alkyl groups having 1 to 20 carbon atoms in $R^1$. Examples of an alkyl group in which at least one hydrogen atom constituting the alkyl group has been replaced by a halogen atom or the like include the same groups as those for the alkyl groups in $R^1$.

Specific examples of —N($R^{10}$)($R^{11}$) include an acylamino group, an ethylcarbonylamino group, a n-propylcarbonylamino group, an isopropylcarbonylamino group, a n-butylcarbonylamino group, an isobutylcarbonylamino group, a tert-butylcarbonylamino group, a n-pentylcarbonylamino group, an isopentylcarbonylamino group, a neopentylcarbonylamino group, a n-hexylcarbonylamino group, a n-heptylcarbonylamino group, a n-octylcarbonylamino group, a n-nonylcarbonylamino group, a n-decylcarbonylamino group, and a trifluoroacylamino group.

A ring containing —N—CO— or —N—SO$_2$— and formed by joining $R^{10}$ and $R^{11}$ together with the nitrogen atom to which they are bonded is preferably a four- to ten-membered ring, and more preferably a five- to seven-membered ring. Specific examples thereof include a 2-pyrrolidone-1-yl group.

$R^1$ is an alkyl group which has 1 to 10 carbon atoms and may have a halogen atom (preferably a fluorine atom), an alkyl group which has 1 to 20 carbon atoms and in which —O— is inserted between carbon atoms constituting the alkyl group, an alkoxy group which has 1 to 10 carbon atoms and may have a halogen atom (preferably a fluorine atom), an alkoxy group which has 1 to 20 carbon atoms and in which —O— is inserted between carbon atoms constituting the alkoxy group, an acyl group which has 1 to 10 carbon atoms and may have a halogen atom (preferably a fluorine atom), an alkoxycarbonyl group which has 2 to 10 carbon atoms and may have a halogen atom (preferably a fluorine atom), an acyloxy group which has 1 to 10 carbon atoms and may have a halogen atom (preferably a fluorine atom), or —N($R^{10}$)($R^{11}$). $R^{10}$ is preferably an acyl group which has 1 to 20 carbon atoms and may have a halogen atom (preferably a fluorine atom). $R^{11}$ is preferably a hydrogen atom.

$R^1$ is more preferably a linear alkyl group which has 1 to 10 carbon atoms and may have a fluorine atom, or —N($R^{10}$)($R^{11}$). $R^{10}$ is more preferably an acyl group which has 1 to 10 carbon atoms and may have a fluorine atom. $R^{11}$ is preferably a hydrogen atom.

$R^1$ is particularly preferably a linear alkyl group which has 1 to 10 carbon atoms and may have a fluorine atom.

In each of two phenylene groups in formula (1), at least one hydrogen atom constituting the phenylene group may be substituted with a substituent $R^7$ or $R^8$ other than hydrogen. $R^7$ and $R^8$ each independently represent an alkyl group having 1 to 4 carbon atoms, an alkoxy group having 1 to 4 carbon atoms, a halogen atom, or a cyano group. $R^7$ and $R^8$ each may be substituted with a hydrogen atom at any position of the phenylene group.

Examples of the alkyl group having 1 to 4 carbon atoms include unsubstituted, linear or branched alkyl groups, such as a methyl group, an ethyl group, a n-propyl group, an isopropyl group, a n-butyl group, an isobutyl group, and a tert-butyl group.

At least one hydrogen atom constituting the alkyl group having 1 to 4 carbon atoms may be substituted with a halogen atom such as a fluorine atom, or a hydroxy group. Examples thereof include haloalkyl groups having 1 to 4 carbon atoms, such as a fluoromethyl group, a trifluoromethyl group, a pentafluoroethyl group, and a nonafluorobutyl group; and hydroxyalkyl groups having 1 to 4 carbon atoms, such as a hydroxymethyl group and a 2-hydroxyethyl group.

Examples of the alkoxy group having 1 to 4 carbon atoms include unsubstituted, linear or branched alkoxy groups, such as a methoxy group, an ethoxy group, a n-propoxy group, an isopropoxy group, a n-butoxy group, an isobutoxy group, and a tert-butoxy group.

At least one hydrogen atom constituting the alkoxy group having 1 to 4 carbon atoms may be substituted with a halogen atom such as a fluorine atom, or a hydroxy group. Examples thereof include haloalkoxy groups having 1 to 4 carbon atoms, such as a fluoromethoxy group, a trifluoromethoxy group, a pentafluoroethoxy group, and a nonafluorobutoxy group; and hydroxyalkoxy groups having 1 to 4 carbon atoms, such as a hydroxymethoxy group and a 2-hydroxyethoxy group.

In formula (1), $R^2$ represents an acyl group having 1 to 20 carbon atoms, an alkylsulfonyl group having 1 to 20 carbon atoms, or an arylsulfonyl group having 6 to 20 carbon atoms, and $R^3$ represents a hydrogen atom or an alkyl group having 1 to 20 carbon atoms. $R^2$ and $R^1$ may be joined together to form a ring containing —N—CO— or —N—SO$_2$— together with the nitrogen atom to which they are bonded. At least one hydrogen atom constituting the acyl group, the alkylsulfonyl group, and the arylsulfonyl group may be substituted with a halogen atom (such as a fluorine atom), a hydroxy group, an amino group, or an amino group having a substituent. Examples of the amino group having a substituent include amino groups substituted with one or two alkyl groups having 1 to 20 carbon atoms, such as an N-methylamino group, an N-ethylamino group, an N,N-dimethylamino group, and an N,N-diethylamino group. —O— or —NR$^{21}$— may be inserted between carbon atoms constituting the alkyl group and the alkoxy group, wherein $R^{21}$ represents a hydrogen atom or an alkyl group having 1 to 20 carbon atoms; and Examples of the acyl group having 1 to 20 carbon atoms in $R^2$ include the same groups as those for the acyl groups in $R^1$.

Examples of the alkylsulfonyl group having 1 to 20 carbon atoms and the arylsulfonyl group having 6 to 20 carbon atoms in $R^2$ include the same groups as those for the alkylsulfonyl groups having 1 to 20 carbon atoms and the same groups as those for the arylsulfonyl groups having 6 to 20 carbon atoms in $R^{10}$, respectively.

A ring containing —N—CO— or —N—SO$_2$— and formed by joining $R^2$ and $R^3$ together with the nitrogen atom to which they are bonded is preferably a four- to ten-membered ring, and more preferably a five- to seven-membered ring. Specific examples thereof include a 2-pyrrolidone-1-yl group.

Examples of the alkyl group having 1 to 20 carbon atoms in $R^{21}$ include the same groups as those described above.

$R^2$ is preferably an acyl group which has 1 to 20 carbon atoms and may have a halogen atom (preferably a fluorine atom) or an alkylsulfonyl group which has 1 to 20 carbon atoms and may have a halogen atom (preferably a fluorine atom), and more preferably an acyl group which has 1 to 10 carbon atoms and may have a fluorine atom or an alkylsulfonyl group which has 1 to 10 carbon atoms and may have a fluorine atom.

$R^3$ is preferably a hydrogen atom.

In formula (1), Y represents a group of formula (Y1):

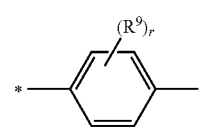

(Y1)

wherein * represents a bonding site with N; $R^9$ is a substituent other than a hydrogen atom, independently represents an alkyl group having 1 to 4 carbon atoms, an alkoxy group having 1 to 4 carbon atoms, a halogen atom, or a cyano group, at least one hydrogen atom constituting the alkyl group having 1 to 4 carbon atoms and the alkoxy group having 1 to 4 carbon atoms may be substituted with a halogen atom or a hydroxy group; r is an integer from 0 to 2, or a group of formula (Y2):

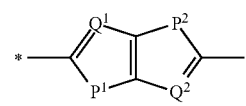

(Y2)

wherein * represents a bonding site with N; $P^1$ and $P^2$ each independently represent —S—, —O—, or —N($R^{12}$)—, wherein $R^{12}$ represents a hydrogen atom or an alkyl group having 1 to 4 carbon atoms; and $Q^1$ and $Q^2$ each independently represent =N— or =CH—.

Examples of $R^9$ include the same groups as those exemplified in $R^7$ and $R^8$.

$P^1$ is preferably —S—.

$P^2$ is preferably —S—.

Examples of the alkyl group having 1 to 4 carbon atoms in $R^1$ include a methyl group, an ethyl group, a n-propyl group, an isopropyl group, a n-butyl group, an isobutyl group, and a tert-butyl group.

$Q^1$ is preferably =CH—.

$Q^2$ is preferably =N—.

p, q, and r in formula (1) are each independently an integer from 0 to 2, and preferably 0.

Specific examples of compound (1) include compounds represented by the following formulae (1-1) to (1-24):

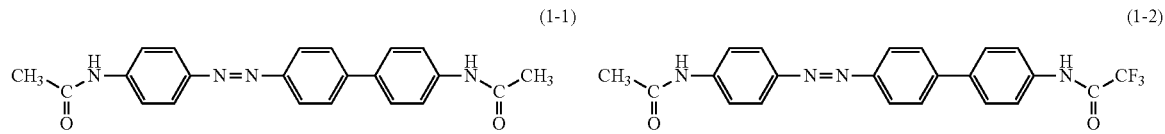
(1-1)  (1-2)

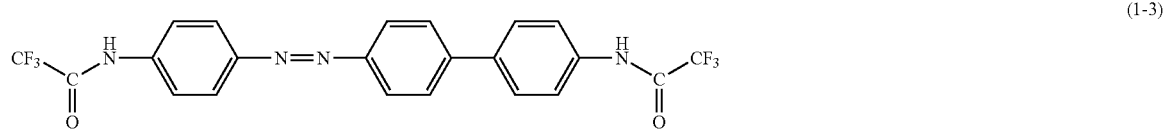
(1-3)

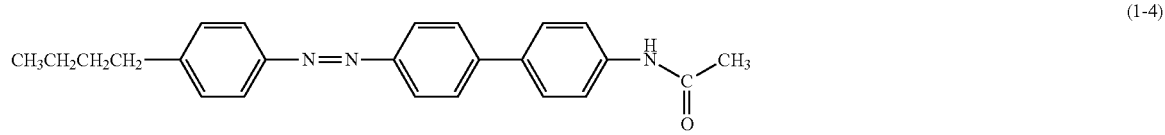
(1-4)

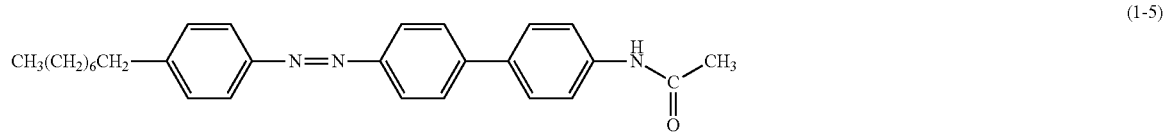
(1-5)

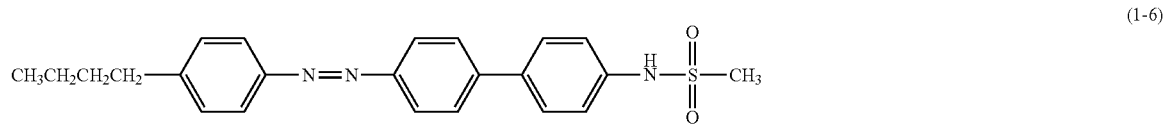
(1-6)

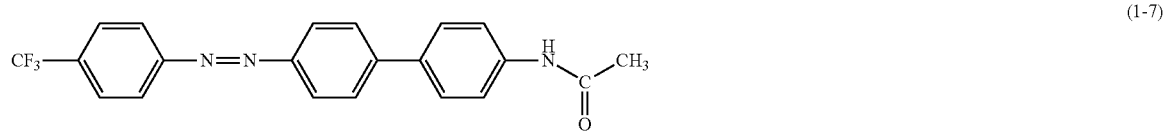
(1-7)

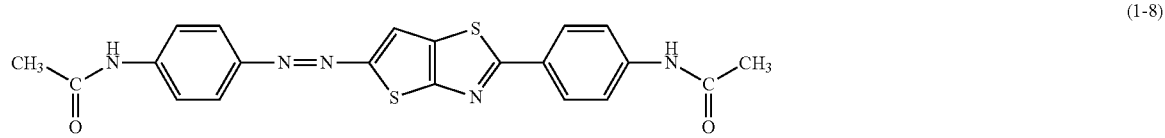
(1-8)

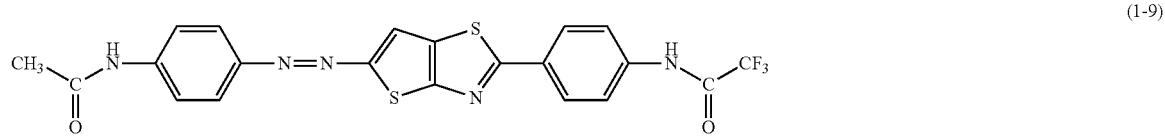
(1-9)

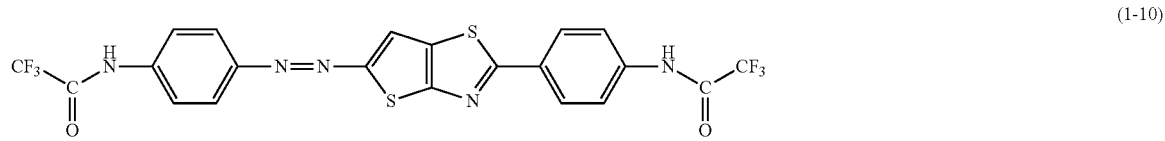
(1-10)

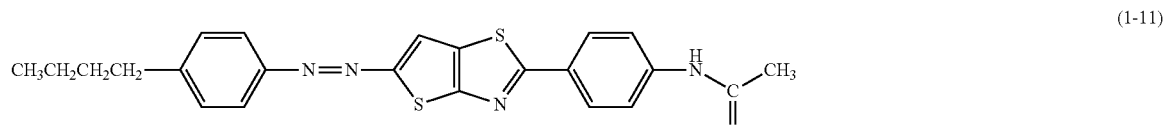
(1-11)

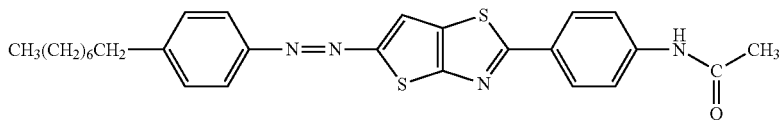
(1-12)

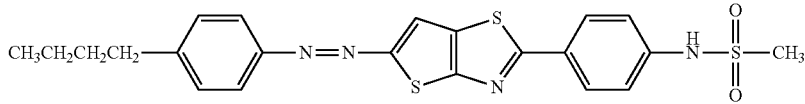
(1-13)

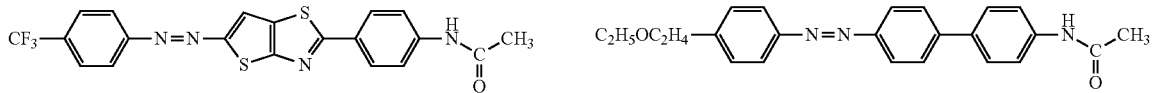
(1-14) (1-15)

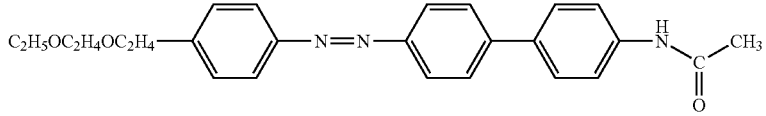
(1-16)

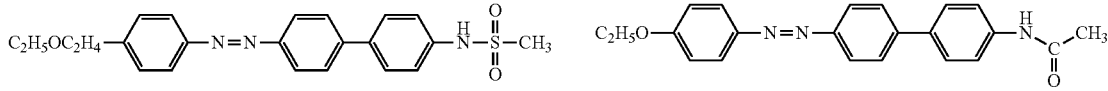
(1-17) (1-18)

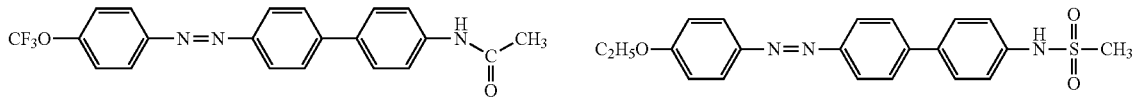
(1-19) (1-20)

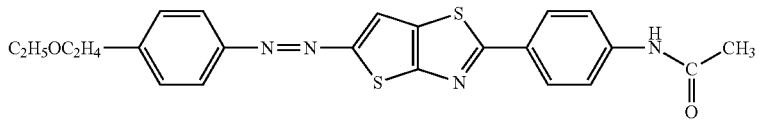
(1-21)

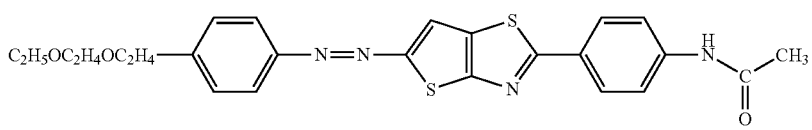
(1-22)

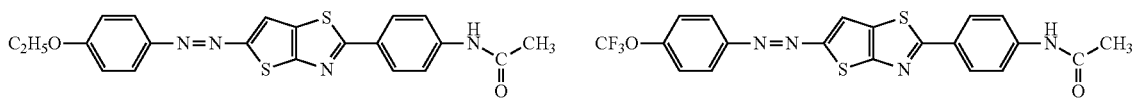
(1-23) (1-24)

Among compounds (1) exemplified above, the compounds represented by formulae (1-1), (1-4), (1-11), and (1-12) are preferable, and the compounds represented by formulae (1-4) and (1-12) are more preferable.

Compound (1) can be produced by reacting a compound represented by formula (2) (hereinafter, may also be referred to as compound (2)):

$$R^1-\text{Ar}(R^7)_p-N=N-Y-X \quad (2)$$

wherein X represents a chlorine atom, a bromine atom, or an iodine atom; and $R^1$, $R^7$, p, and Y are respectively the same meaning as above, with a compound represented by formula (3) (hereinafter, may also be referred to as compound (3)):

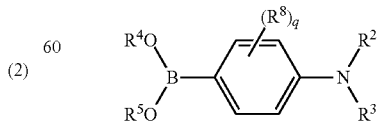

wherein $R^2$, $R^3$, $R^8$, and q are respectively the same meaning as above; $R^4$ and $R^5$ each independently represent a hydrogen atom or an alkyl group having 1 to 10 carbon atoms, and $R^4$ and $R^5$ may be joined together to form a ring containing —O—B—O—together with the oxygen atom and the boron atom to which they are bonded.

X in compound (2) is preferably a bromine atom.

Examples of the alkyl group having 1 to 10 carbon atoms and represented by $R^4$ and the alkyl group having 1 to 10 carbon atoms and represented by $R^5$ in compound (3) include unsubstituted, linear or branched alkyl groups having 1 to 10 carbon atoms, such as a methyl group, an ethyl group, a n-propyl group, an isopropyl group, a n-butyl group, an isobutyl group, a tert-butyl group, a n-pentyl group, an isopentyl group, a neopentyl group, a n-hexyl group, a n-heptyl group, a n-octyl group, a n-nonyl group, and a n-decyl group.

Examples of the ring containing —O—B—O— and formed by joining $R^4$ and $R^5$ together with the oxygen atom and the boron atom to which they are bonded include the following rings. In the following formulae, * represents a bond to a benzene ring.

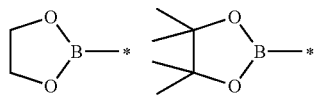

Examples of —B(OR$^4$)(OR$^5$) include the following groups, and —B(OH)$_2$ is preferable.
In the following formulae, * represents a bond to a benzene ring.

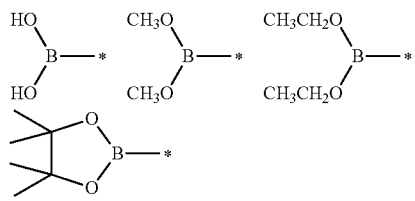

Compound (2) may be a commercially available product or may be synthesized according to the method described in Synthesis, 1997, 6, 681 or Journal of Chemical Society, 1970, 35, 505. Compound (2) may be synthesized by Sandmeyer reaction from an aminated compound synthesized in accordance with the method described in JP-A-S58-38756. The Sandmeyer reaction can be carried out by the method described in Journal of Chemical society, Perkin Trans. 1998, 685.

Specific examples of compound (2) include compounds represented by the following formulae (2-1) to (2-18):

(2-1)
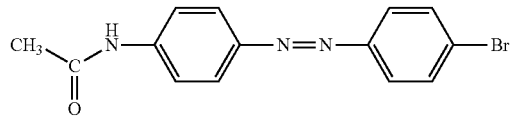

(2-2)
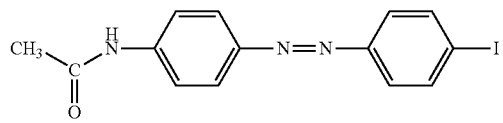

(2-3)
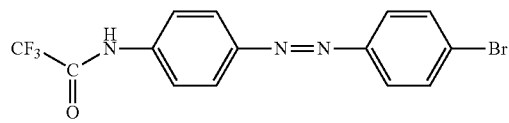

(2-4)
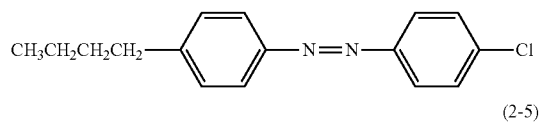

(2-5)
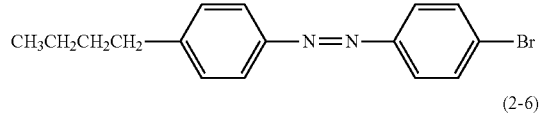

(2-6)
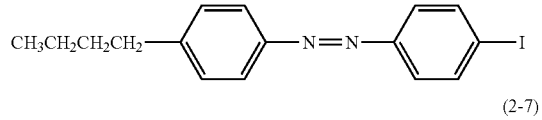

(2-7)
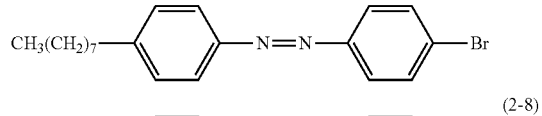

(2-8)
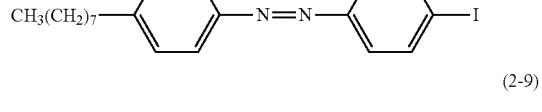

(2-9)
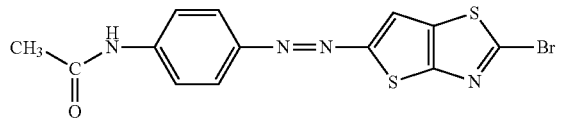

(2-10)
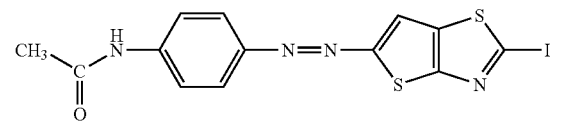

(2-11)
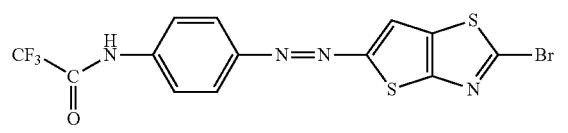

(2-12)
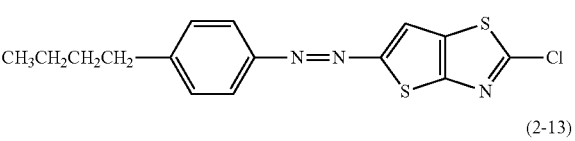

(2-13)
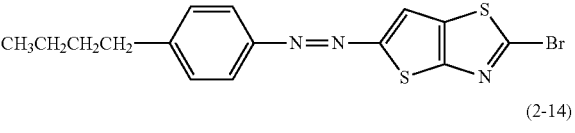

(2-14)

(2-15)
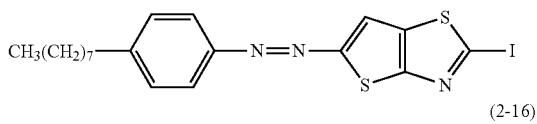

(2-16)
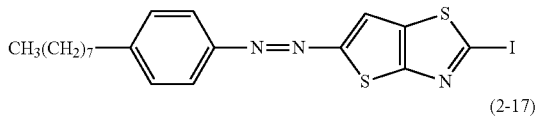

(2-17)
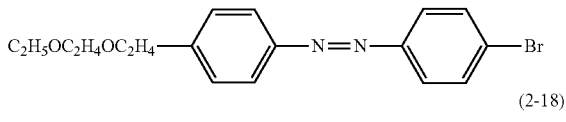

(2-18)
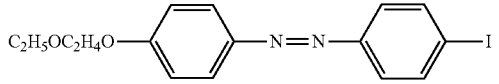

Specific examples of compound (3) include compounds represented by the following formulae (3-1) to (3-7):

(3-1)
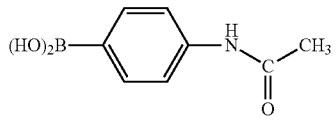

(3-2)
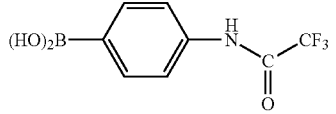

(3-3)
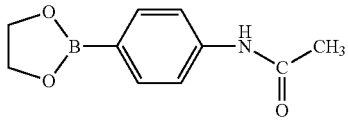

(3-4)
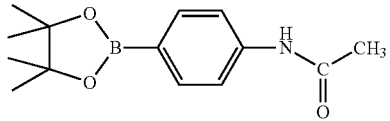

(3-5)
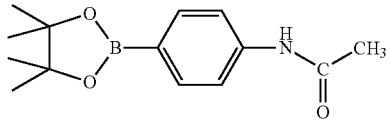

(3-6)
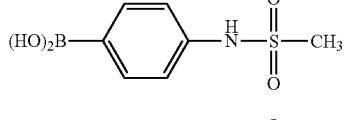

(3-7)
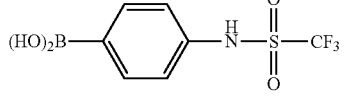

Compound (3) may be a commercially available product or may be synthesized in accordance with the method described in Journal of Organic Chemistry, 1995, 60, 7508.

The reaction of compound (2) with compound (3) can be carried out in accordance with the method described in Chemical Reviews, 1995, 95(7), 2457.

Compound (1) after termination of reaction can be taken out by usual extracting means such as recrystallization, reprecipitation, extraction, and various chromatographies.

Compound (1) functions as a dichroic dye and, particularly when orientated with a polymerizable liquid crystal compound, shows higher dichroism. Accordingly, a polarizing film in which compound (1) is orientated with a polymerizable liquid crystal compound shows higher dichroism. Compound (1) has a maximum absorption in a wavelength range of 350 nm to 510 nm, preferably a wavelength range of 400 nm to 500 nm, more preferably a wavelength range of 410 nm to 490 nm, and still more preferably a wavelength range of 420 nm to 480 nm. Since compound (1) has light resistance, a polarizing film containing the present compound is excellent in light resistance.

The light resistance of the polarizing film can be evaluated by, for example, the following method.

A protective film is disposed on a surface of a formed polarizing film and irradiated with light from the upper side under the following conditions. The light resistance is evaluated from the ratio of the absorbance of a polarizing film at a maximum absorption wavelength of 501 nm of a polarizing film after a light resistance test to the absorbance of the polarizing film at a maximum absorption wavelength of 501 nm of the polarizing film before the test.

For example, when the light resistance test is conducted by forming a polarizing film with the use of a dichroic dye shown by formula (1-10) described in JP-A-2013-101328, the absorbance of the polarizing film after the light resistance test at a maximum absorption wavelength of 548 nm of the polarizing film is 47% as compared to the state before the test.

(Light Irradiation Conditions in Light Resistance Test)

Equipment used: Suntest XLS+ manufactured by Atlas Material Testing Solutions

Light source used: xenon arc lamp

Exposure condition: 250 mW/m$^2$

Test time: 120 hours

Exposure dose: 108000 KJ/m$^2$

Temperature: 60° C.

Subsequently, the present composition containing a polymerizable liquid crystal compound and compound (1) will be described.

The present composition may contain two or more kinds of compounds (1).

<Polymerizable Liquid Crystal Compound>

The polymerizable liquid crystal compound is a compound having a polymerizable group in the molecule and can exhibit a liquid crystal phase by being orientated, and is preferably a compound which can exhibit a liquid crystal phase by being orientated independently.

The polymerizable group means a group involved in polymerization reaction and is preferably a photopolymerizable group. Here, the polymerizable group refers to a group that can be involved in polymerization reaction by an active radial, an acid, or the like generated from a polymerization initiator to be described later. Examples of the polymerizable group include a vinyl group, a vinyloxy group, a 1-chlorovinyl group, an isopropenyl group, a 4-vinylphenyl group, an acryloyloxy group, a methacryloyloxy group, an oxiranyl group, and an oxetanyl group. Among them, an acryloyloxy group, a methacryloyloxy group, a vinyloxy group, an oxiranyl group, and an oxetanyl group are preferable, and an acryloyloxy group is more preferable.

The polymerizable liquid crystal compound may be of a thermotropic liquid-crystal type or a lyotropic liquid-crystal type.

The polymerizable liquid crystal compound may exhibit a nematic liquid crystal phase, a smectic liquid crystal phase, or both a nematic liquid crystal phase and a smectic liquid crystal phase. The polymerizable liquid crystal compound preferably exhibits a smectic liquid crystal phase, and more preferably exhibits a higher order smectic liquid crystal phase. The present composition containing the polymerizable liquid crystal compound exhibiting the smectic liquid crystal phase can provide a polarizing film more excellent in polarizing performance. The present composition may contain two or more kinds of polymerizable liquid crystal compounds.

Compound (1) can exhibit high dichroism even in such a state that it is dispersed between dense molecular chains formed from the polymerizable liquid crystal compound exhibiting the smectic liquid crystal phase, and a composition that contains compound (1) can provide a polarizing film having a high dichroic ratio.

Examples of the higher order smectic liquid crystal phase include a smectic B phase, a smectic D phase, a smectic E phase, a smectic F phase, a smectic G phase, a smectic H phase, a smectic I phase, a smectic J phase, a smectic K phase, and a smectic L phase. Among them, a smectic B phase, a smectic F phase, and a smectic I phase are preferable. When the smectic liquid crystal phase exhibited by the polymerizable liquid crystal compound is such a higher order smectic phase, a polarizing film with higher degree of orientation order can be produced. A polarizing film having high degree of orientation order and obtained from a composition containing a polymerizable liquid crystal compound exhibiting a higher order smectic liquid crystal phase exhibits a Bragg peak derived from a higher order structure such as a hexatic phase or a crystal phase in X-ray diffractometry. The Bragg peak is a peak derived from the periodic structure of molecular orientation. A periodic interval of a polarizing film obtained from the present composition is preferably 3.0 to 5.0 Å (0.30 nm to 0.50 nm).

For example, the kind of the liquid crystal phase exhibited by a polymerizable liquid crystal compound can be confirmed as follows. A suitable substrate is prepared, and a solution containing a polymerizable liquid crystal compound and a solvent is applied onto the substrate to form a coating film. The solvent contained in the coating film is then removed by heat treatment or decompression treatment. Subsequently, a liquid crystal phase developed by heating the coating film formed on the substrate to the isotropic phase transition temperature and gradually cooling the coating film is inspected by texture observation under polarizing microscope, X-ray diffractometry, or differential scanning calorimetry measurement. In this inspection, for example, it can be confirmed that a nematic liquid crystal phase is exhibited by cooling to a first temperature, and a smectic liquid crystal phase is exhibited by further gradually cooling to a second temperature.

The polymerizable liquid crystal composition is preferably a compound represented by formula (4) (hereinafter, may also be referred to as compound (4)):

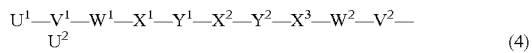

(4)

in formula (4), $X^1$, $X^2$, and $X^3$ each independently represent an optionally substituted 1,4-phenylene group or an optionally substituted cyclohexane-1,4-diyl group, provided that at least one of $X^1$, $X^2$, and $X^3$ is an optionally substituted 1,4-phenylene group; —CH$_2$— constituting the cyclohexane-1,4-diyl group may be replaced by —O—, —S—, or —NR—; R represents an alkyl or phenyl group having 1 to 6 carbon atoms;

$Y^1$ and $Y^2$ each independently represent —CH$_2$CH$_2$—, —CH$_2$O—, —COO—, —OCOO—, a single bond, —N=N—, —CR$^a$=CR$^b$—, —C≡C—, or —CR$^a$=N—; R$^a$ and R$^b$ each independently represent a hydrogen atom or an alkyl group having 1 to 4 carbon atoms;

$U^1$ represents a hydrogen atom or a polymerizable group; $U^2$ represents a polymerizable group;

$W^1$ and $W^2$ each independently represent a single bond, —O—, —S—, —COO—, or —OCOO—; and $V^1$ and $V^2$ each independently represent an optionally substituted alkanediyl group having 1 to 20 carbon atoms, and —CH$_2$— constituting the alkanediyl group may be replaced by —O—, —S—, or —NH—.

In compound (4), at least one of $X^1$, $X^2$, and $X^3$ is preferably an optionally substituted 1,4-phenylene group.

The optionally substituted 1,4-phenylene group is preferably an unsubstituted 1,4-phenylene group. The optionally substituted cyclohexane-1,4-diyl group is preferably an optionally substituted trans-cyclohexane-1,4-diyl group. The optionally substituted trans-cyclohexane-1,4-diyl group is preferably an unsubstituted trans-cyclohexane-1,4-diyl group.

Examples of the substituent group optionally included in the optionally substituted 1,4-phenylene group or the optionally substituted cyclohexane-1,4-diyl group include alkyl groups having 1 to 4 carbon atoms, such as a methyl group, an ethyl group, and a n-butyl group; a cyano group; and a halogen atom.

$Y^1$ is preferably —CH$_2$CH$_2$—, —COO—, or a single bond, and $Y^2$ is preferably —CH$_2$CH$_2$— or —CH$_2$O—.

$U^2$ represents a polymerizable group. $U^1$ is a hydrogen atom or a polymerizable group, and preferably a polymerizable group. Both of $U^1$ and $U^2$ are preferably polymerizable groups, and more preferably photopolymerizable groups. A polymerizable liquid crystal compound having a photo-polymerizable group is advantageous in that the liquid crystal compound can be polymerized in lower temperature conditions.

The polymerizable groups represented by $U^1$ and $U^2$ may be different from each other, but are preferably the same. Examples of the polymerizable group include a vinyl group, a vinyloxy group, a 1-chlorovinyl group, an isopropenyl group, a 4-vinylphenyl group, an acryloyloxy group, a methacryloyloxy group, an oxiranyl group, and an oxetanyl group. Among them, an acryloyloxy group, a methacryloyloxy group, a vinyloxy group, an oxiranyl group, and an oxetanyl group are preferable, and an acryloyloxy group is more preferable.

Examples of the alkanediyl group represented by $V^1$ and $V^2$ include a methylene group, an ethylene group, a propane-1,3-diyl group, a butane-1,3-diyl group, a butane-1,4-diyl group, a pentane-1,5-diyl group, a hexane-1,6-diyl group, a heptane-1,7-diyl group, an octane-1,8-diyl group, a decane-1,10-diyl group, a tetradecane-1,14-diyl group, and an eicosane-1,20-diyl group. Each of $V^1$ and $V^2$ is preferably an alkanediyl group having 2 to 12 carbon atoms, and more preferably an alkanediyl group having 6 to 12 carbon atoms.

Examples of the substituent group optionally included in the optionally substituted alkanediyl group having 1 to 20 carbon atoms include a cyano group and a halogen atom. The alkanediyl group is preferably an unsubstituted alkanediyl group, and more preferably an unsubstituted and linear alkanediyl group.
$W^1$ and $W^2$ are each independently and preferably a single bond or —O—.
Specific examples of compound (4) include compounds represented by the following formulae (4-1) to (4-43). When compound (4) has a cyclohexane-1,4-diyl group, the cyclohexane-1,4-diyl group is preferably a trans type.
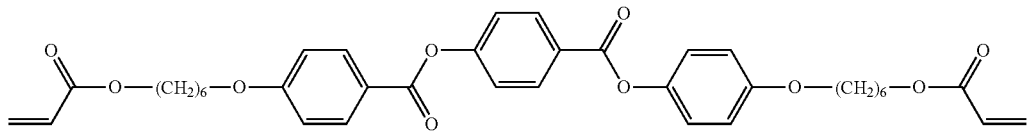
(4-1)
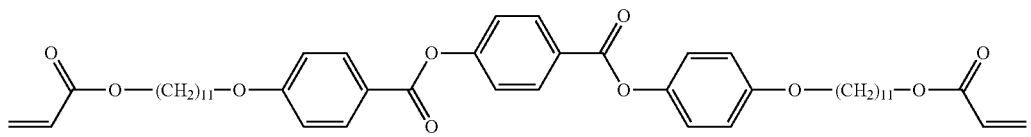
(4-2)
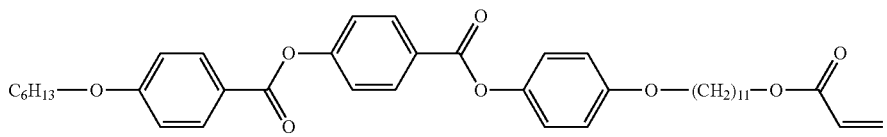
(4-3)
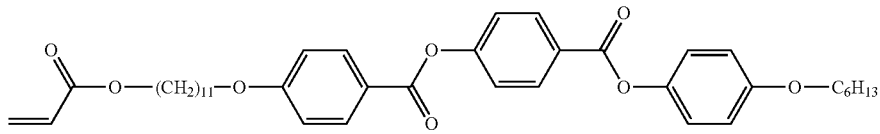
(4-4)
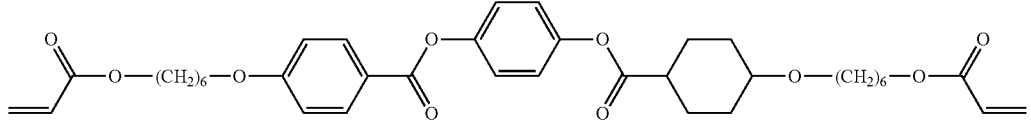
(4-5)
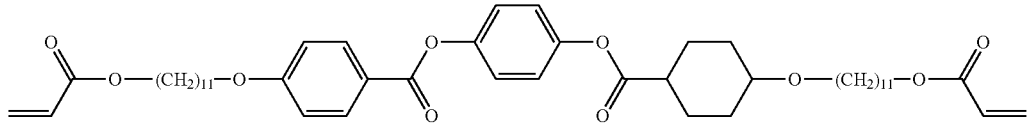
(4-6)
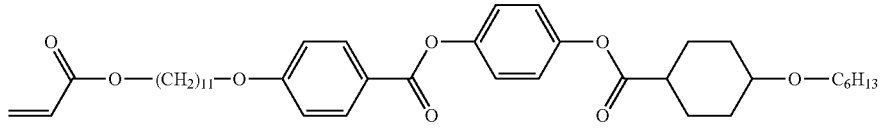
(4-7)
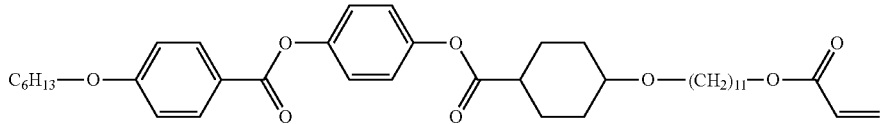
(4-8)
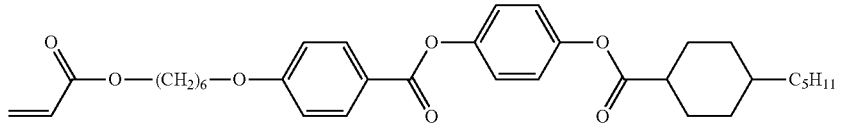
(4-9)
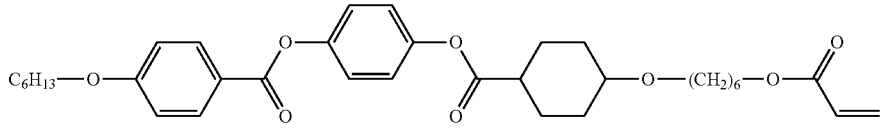
(4-10)

(4-11)
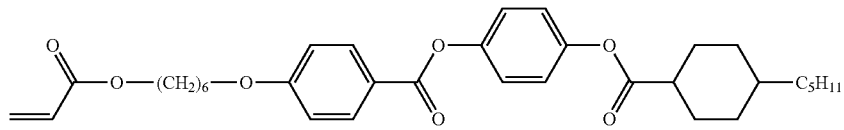
(4-12)
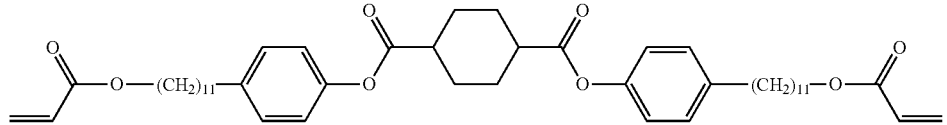
(4-13)
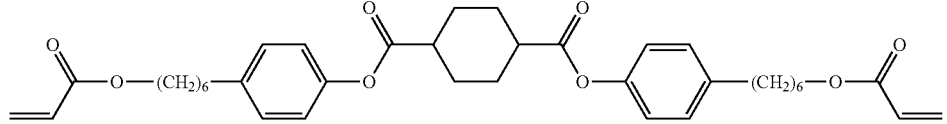
(4-14)
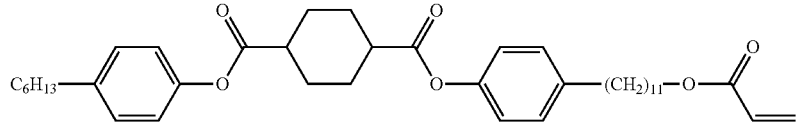
(4-15)
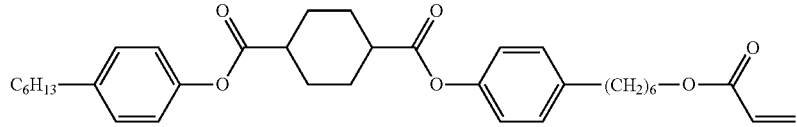
(4-16)
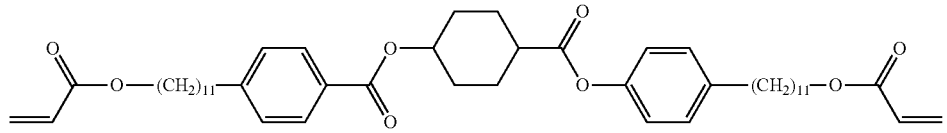
(4-17)
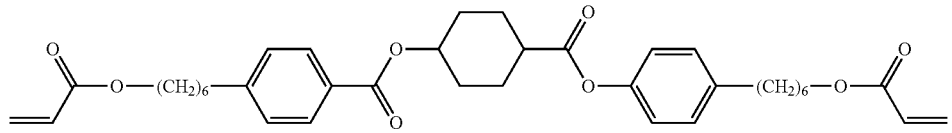
(4-18)
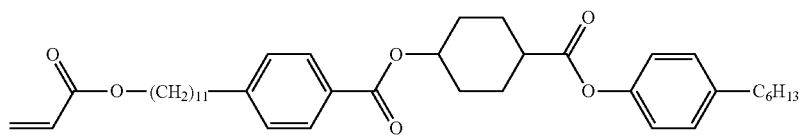
(4-19)
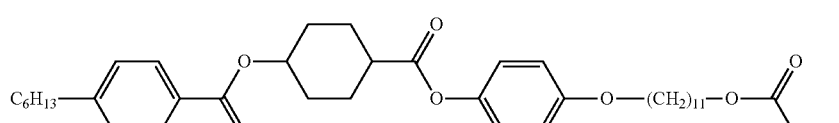
(4-20)
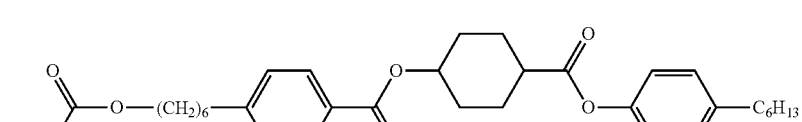
(4-21)
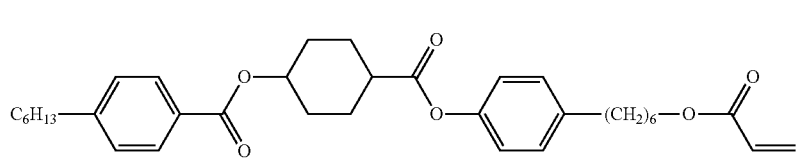

-continued
(4-22)
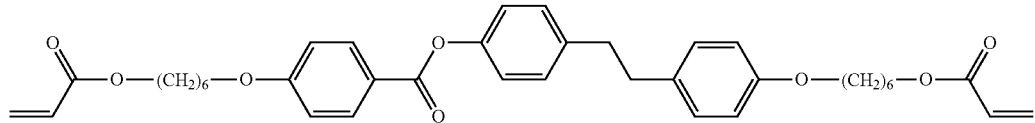
(4-23)
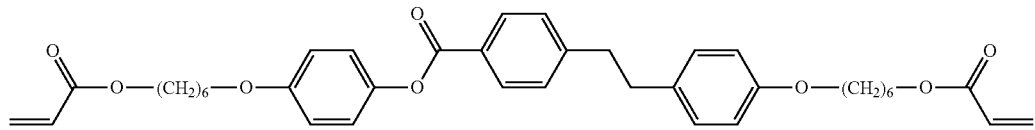
(4-24)
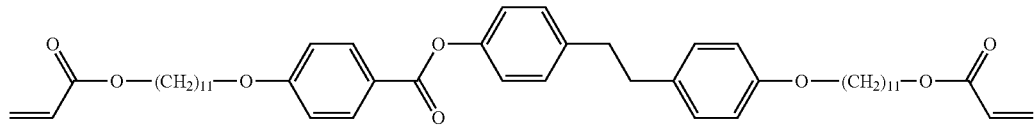
(4-25)
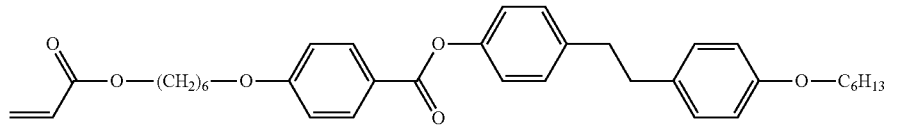
(4-26)
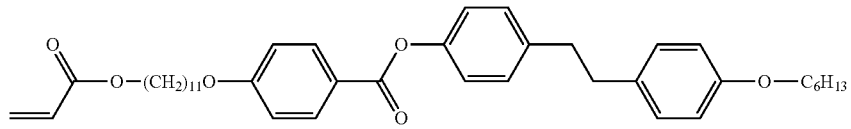
(4-27)
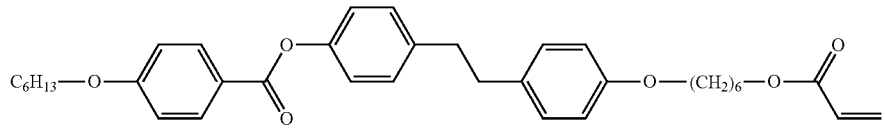
(4-28)
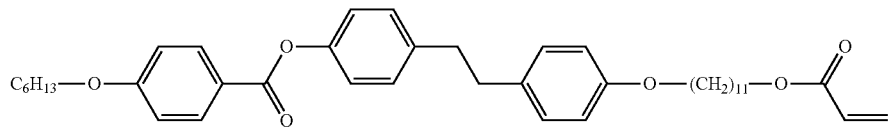
(4-29)
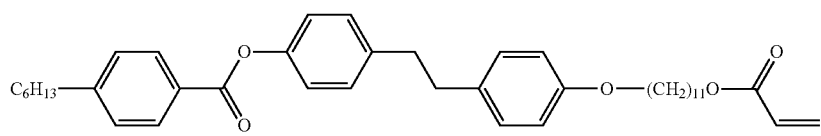
(4-30)
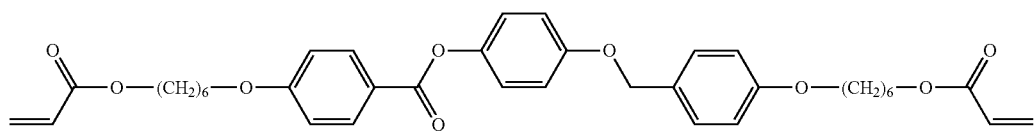
(4-31)
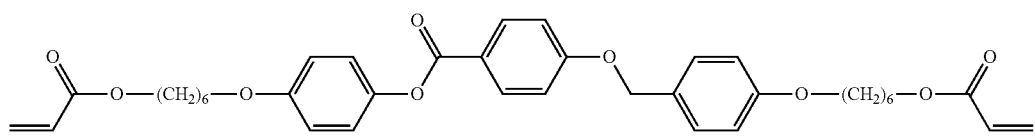
(4-32)
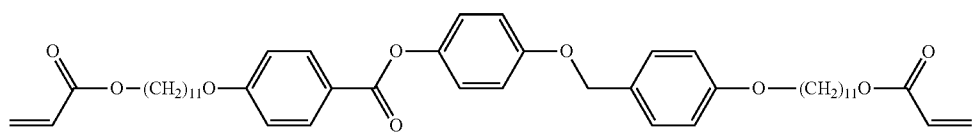

-continued
(4-33)
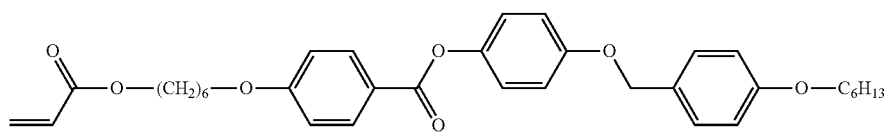
(4-34)
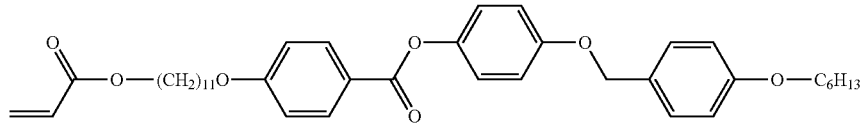
(4-35)
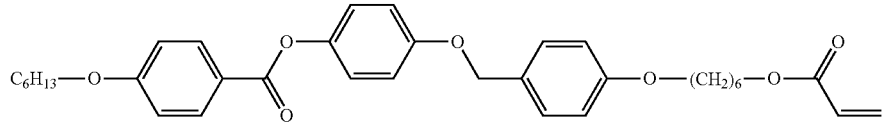
(4-36)
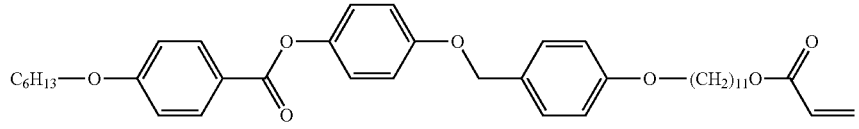
(4-37)
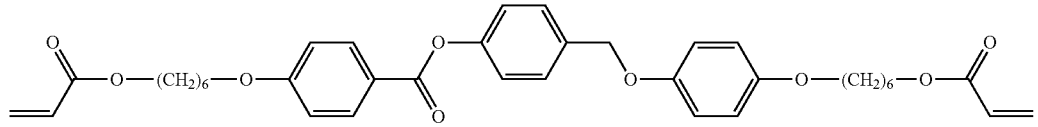
(4-38)
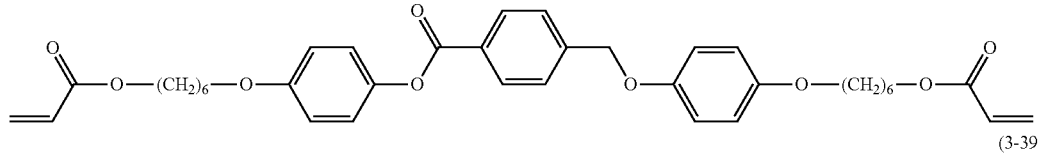
(3-39)
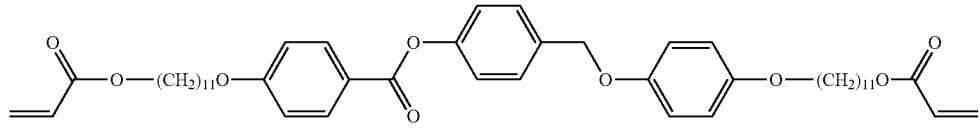
(4-40)
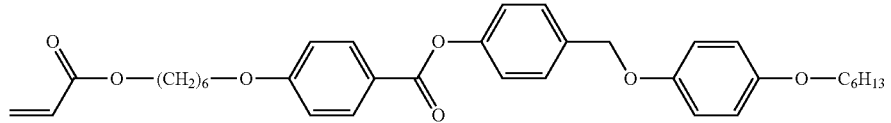
(4-41)
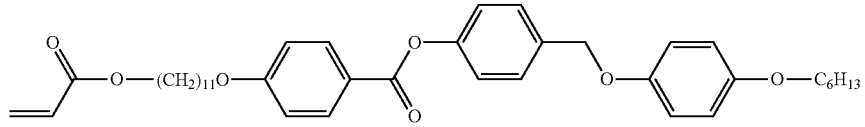
(4-42)
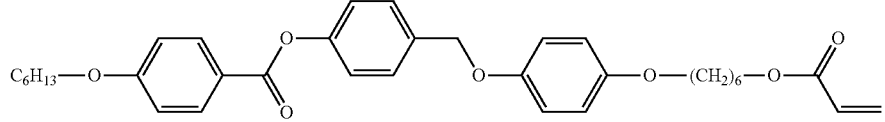
(4-43)
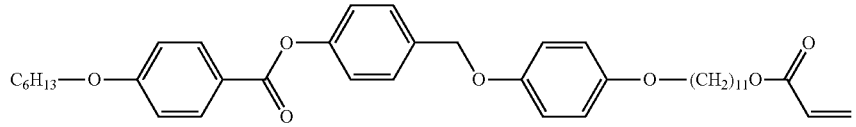

Among compounds (4) exemplified above, preferred is at least one compound selected from the group consisting of the compounds represented by formula (4-5), formula (4-6), formula (4-7), formula (4-8), formula (4-9), formula (4-10), formula (4-11), formula (4-12), formula (4-13), formula (4-14), formula (4-15), formula (4-22), formula (4-24), formula (4-25), formula (4-26), formula (4-27), formula (4-28), and formula (4-29).

The present composition may contain two or more kinds of compounds (4). When two or more kinds of polymerizable liquid crystal compounds are used in combination, it is preferable that at least one kind compound is compound (4), and it is more preferable that two or more kind compounds are compounds (4). Combination of the compounds may make it possible to temporarily keep the liquid crystal phase even at a temperature not more than the liquid crystal-crystal phase transition temperature. The mixing ratio in the case of combination of two kinds of polymerizable liquid crystal compounds is usually 1:99 to 50:50, preferably 5:95 to 50:50, and more preferably 10:90 to 50:50.

Compound (4) can be produced by, for example, a method described in conventionally known documents such as Lub et al. Recl. Trav. Chim. Pays-Bas, 115, 321-328 (1996) or Japanese Patent No. 4719156.

From the viewpoint of improvement in orientation of the polymerizable liquid crystal compound, the content of the polymerizable liquid crystal compound in the present composition is preferably 70 to 99.5 parts by mass, more preferably 80 to 99 parts by mass, still more preferably 80 to 94 parts by mass, and particularly preferably 80 to 90 parts by mass based on 100 parts by mass of the solid matter of the present composition. Herein, the solid matter means the total amount of components other than the solvent in the present composition.

The present composition preferably contains a polymerization initiator and a solvent, and may contain a photosensitizer, a polymerization inhibitor, and a leveling agent.

The content of compound (1) in the present composition is usually not more than 50 parts by mass, preferably not less than 0.1 parts by mass and not more than 10 parts by mass, and more preferably not less than 0.1 parts by mass and not more than 5 parts by mass based on 100 parts by mass of the polymerizable liquid crystal compound. When the content of compound (1) is not more than 50 parts by mass based on 100 parts by mass of the polymerizable liquid crystal compound, there is a tendency that a polarizing film having small orientation disorder for the polymerizable liquid crystal compound and compound (1) can be obtained.

<Solvent>

The solvent is preferably a solvent which can completely dissolve the polymerizable liquid crystal compound and compound (1) therein and which is inactive on the polymerization reaction of the polymerizable liquid crystal compound.

Examples of the solvent include alcohol solvents such as methanol, ethanol, ethylene glycol, isopropyl alcohol, propylene glycol, ethylene glycol methyl ether, ethylene glycol butyl ether, and propylene glycol monomethyl ether; ester solvents such as ethyl acetate, butyl acetate, ethylene glycol methyl ether acetate, γ-butyrolactone, propylene glycol methyl ether acetate, and ethyl lactate; ketone solvents such as acetone, methyl ethyl ketone, cyclopentanone, cyclohexanone, 2-heptanone, and methyl isobutyl ketone; aliphatic hydrocarbon solvents such as pentane, hexane, and heptane; aromatic hydrocarbon solvents such as toluene and xylene; nitrile solvents such as acetonitrile; ether solvents such as tetrahydrofuran and dimethoxyethane; and chlorine-containing solvents such as chloroform and chlorobenzene. These solvents may be used alone or in combination.

When the present composition contains a solvent, the content of the solvent is preferably 50 to 98% by mass to the total amount of the present composition. In other words, the amount of the solid matter in the present composition is preferably 2 to 50% by mass. If the amount of the solid matter is not more than 50% by mass, the viscosity of the present composition is lowered so that the thickness of a polarizing film obtained from the present composition is made approximately uniform, and thus the polarizing film tends to be hardly uneven. The amount of the solid matter can be determined in consideration of the thickness of the polarizing film to be produced.

<Polymerization Initiator>

The polymerization initiator is a compound which can cause polymerization reaction of a polymerizable liquid crystal compound. The polymerization initiator is preferably a photopolymerization initiator which can generate active radicals by light action.

Examples of the polymerization initiator include a benzoin compound, a benzophenone compound, an alkylphenone compound, an acylphosphine oxide compound, a triazine compound, an iodonium salt, and a sulfonium salt.

Examples of the benzoin compound include benzoin, benzoin methyl ether, benzoin ethyl ether, benzoin isopropyl ether, and benzoin isobutyl ether.

Examples of the benzophenone compound include benzophenone, methyl o-benzoylbenzoate, 4-phenylbenzophenone, 4-benzoyl-4'-methyldiphenyl sulfide, 3,3',4,4'-tetra(tert-butylperoxycarbonyl)benzophenone, and 2,4,6-trimethylbenzophenone.

Examples of the alkylphenone compound include oligomers of diethoxyacetophenone, 2-methyl-2-morpholino-1-(4-methylthiophenyl)propan-1-one, 2-benzyl-2-dimethylamino-1-(4-morpholinophenyl)butan-1-one, 2-hydroxy-2-methyl-1-phenylpropan-1-one, 1,2-diphenyl-2,2-dimethoxyethan-1-one, 2-hydroxy-2-methyl-1-[4-(2-hydroxyethoxy)phenyl]propan-1-one, 1-hydroxycyclohexyl phenyl ketone, and 2-hydroxy-2-methyl-1-[4-(1-methylvinyl)phenyl]propan-1-one.

Examples of the acylphosphine oxide compound include 2,4,6-trimethylbenzoyldiphenylphosphine oxide and bis(2,4,6-trimethylbenzoyl)phenylphosphine oxide.

Examples of the triazine compound include 2,4-bis(trichloromethyl)-6-(4-methoxyphenyl)-1,3,5-triazine, 2,4-bis(trichloromethyl)-6-(4-methoxynaphthyl)-1,3,5-triazine, 2,4-bis(trichloromethyl)-6-(4-methoxystyryl)-1,3,5-triazine, 2,4-bis(trichloromethyl)-6-[2-(5-methylfuran-2-yl)ethenyl]-1,3,5-triazine, 2,4-bis(trichloromethyl)-6-[2-(furan-2-yl)ethenyl]-1,3,5-triazine, 2,4-bis(trichloromethyl)-6-[2-(4-diethylamino-2-methylphenyl)ethenyl]-1,3,5-triazine, and 2,4-bis(trichloromethyl)-6-[2-(3,4-dimethoxyphenyl)ethenyl]-1,3,5-triazine.

Examples of the iodonium salt and the sulfonium salt include salts represented by the following formulae.

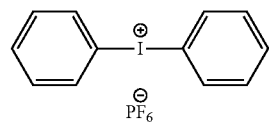

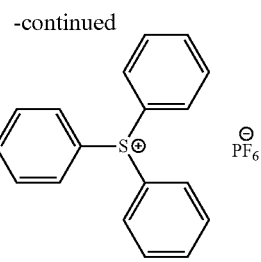

Only one kind of the polymerization initiator may be used, or two or more kinds of the polymerization initiators may be used in combination.

Commercially available polymerization initiator may be used. Examples of the commercially available polymerization initiator include Irgacure (registered trademark) 907, 184, 651, 819, 250, and 369 (manufactured by Ciba Specialty Chemicals Corp.); SEIKUOL (registered trademark) BZ, Z, and BEE (manufactured by Seiko Chemical Co., Ltd.); Kayacure (registered trademark) BP100 and UVI-6992 (manufactured by The Dow Chemical Company); ADEKA OPTOMER SP-152 and SP-170 (manufactured by ADEKA); TAZ-A and TAZ-PP (manufactured by Nihon SiberHegner K.K.); and TAZ-104 (manufactured by Sanwa Chemical Co., Ltd.).

When the present composition contains a polymerization initiator, the content of the polymerization initiator in the present composition is usually 0.1 to 30 parts by mass, preferably 0.5 to 10 parts by mass, and more preferably 0.5 to 8 parts by mass based on 100 parts by mass of the polymerizable liquid crystal compound, from the viewpoint of hardly causing orientation disorder for the polymerizable liquid crystal compound.

<Photosensitizer>

When the present composition contains a photopolymerization initiator, the present composition preferably contains a photosensitizer. When the present composition contains a polymerization initiator and a photosensitizer, the polymerization reaction of the polymerizable liquid crystal compound tends to be promoted. Examples of the photosensitizer include xanthone compounds such as xanthone and thioxanthone (e.g., 2,4-diethylthioxanthone and 2-isopropylthioxanthone); anthracene compounds such as anthracene and alkoxy group-containing anthracene (e.g., dibutoxyanthracene); phenothiazine and rubrene.

When the present composition contains a photosensitizer, the content of the photosensitizer in the present composition is preferably 0.1 to 30 parts by mass, more preferably 0.5 to 10 parts by mass, and still more preferably 0.5 to 8 parts by mass based on 100 parts by mass of the polymerizable liquid crystal compound.

<Polymerization Inhibitor>

Examples of the polymerization inhibitor include radical scavengers such as hydroquinone, alkoxy group-containing hydroquinone, alkoxy group-containing catechol (e.g., butylcatechol), pyrogallol, 2,2,6,6-tetramethyl-1-piperidinyl oxyradical; thiophenols; β-naphthylamines; and β-naphthols.

When the present composition contains a polymerization inhibitor, the polymerization inhibitor can control the promotion degree of the polymerization reaction of the polymerizable liquid crystal compound.

When the present composition contains a polymerization inhibitor, the content of the polymerization inhibitor in the present composition is preferably 0.1 to 30 parts by mass, more preferably 0.5 to 10 parts by mass, and still more preferably 0.5 to 8 parts by mass based on 100 parts by mass of the polymerizable liquid crystal compound.

<Leveling Agent>

The leveling agent has a function of adjusting the fluidity of the present composition and making a coating film, which is obtained by application of the present composition, flatter. Examples thereof may include a surfactant. Examples of a preferable leveling agent are a leveling agent mainly composed of a polyacrylate compound and a leveling agent mainly composed of a fluorine atom-containing compound.

Examples of the leveling agent mainly composed of a polyacrylate compound include BYK-350, BYK-352, BYK-353, BYK-354, BYK-355, BYK-358N, BYK-361N, BYK-380, BYK-381, and BYK-392 (manufactured by BYK-Chemie GmbH).

Examples of the leveling agent mainly composed of a fluorine atom-containing compound include Megafac (registered trademark) R-08, R-30, R-90, F-410, F-411, F-443, F-445, F-470, F-471, F-477, F-479, F-482, and F-483 (manufactured by DIC Corporation); SURFLON (registered trademark) S-381, S-382, S-383, S-393, SC-101, SC-105, KH-40, and SA-100 (manufactured by AGC Seimi Chemical Co., Ltd.); E1830 and E5844 (manufactured by Daikin Fine Chemical Co., Ltd.); and EFTOP EF301, EF303, EF351, and EF352 (manufactured by Mitsubishi Materials Electronic Chemicals Co., Ltd.).

When the present composition contains a leveling agent, the content of the leveling agent is preferably not less than 0.3 parts by mass and not more than 5 parts by mass, and more preferably not less than 0.5 parts by mass and not more than 3 parts by mass based on 100 parts by mass of the polymerizable liquid crystal compound.

When the content of the leveling agent is within the above-mentioned range, it is made easy to horizontally orientate the polymerizable liquid crystal compound, and a polarizing film to be obtained tends to be smoother. If the content of the leveling agent to the polymerizable liquid crystal compound exceeds the above-mentioned range, a polarizing film to be obtained easily tends to be uneven. The present composition may contain two or more kinds of leveling agents.

<Process for Producing Polarizing Film>

A polarizing film containing compound (1) can be obtained by, for example, application of the present composition. Preferably, the polarizing film can be produced by a production process including the following steps (A) to (C).

Step (A): a step of applying the present composition to a surface of a substrate or a substrate having an orientation film formed thereon Step (B): a step of orientating a polymerizable liquid crystal compound and compound (1) contained in the formed coating film Step (C): a step of irradiating the orientated polymerizable liquid crystal compound with an active energy ray to polymerize the polymerizable liquid crystal compound <Step (A)>

<Substrate>

The substrate may be a glass substrate or a resin substrate, and preferably a resin substrate. A thin polarizing plate can be obtained by using a film substrate formed of a resin.

The resin substrate is preferably a transparent resin substrate. The transparent resin substrate means a substrate having translucency for transmitting light, particularly visible light, and the translucency means a characteristic of a visibility correction transmittance of not less than 80% for light rays with a wavelength of 380 nm to 780 nm.

The substrate is preferably a retardation film having the ¼ wavelength plate function (hereinafter, may also be referred to as a ¼ wavelength plate). A circularly polarizing plate can be obtained by using a ¼ wavelength plate as the substrate.

In this case, it is preferable to perform stacking such that an angle between the transmission axis of the polarizing film and the slow axis (optical axis) of the ¼ wavelength plate is substantially 450. The phrase substantially 45° usually denotes a range of 45±50. When the optical axes of the polarizing film and the ¼ wavelength plate are aligned or are orthogonal to each other, a polarizing film functioning as an optical compensation film can be obtained.

The ¼ wavelength plate usually has optical characteristics represented by formula (40) and preferably has optical characteristics represented by formula (40-1).

$$100 \text{ nm} < Re(550) < 160 \text{ nm} \tag{40}$$

$$130 \text{ nm} < Re(550) < 150 \text{ nm} \tag{40-1}$$

wherein Re(550) represents an in-plane retardation value for light with a wavelength of 550 nm.

The ¼ wavelength plate preferably has reverse wavelength dispersion characteristics. The reverse wavelength dispersion characteristics mean that an in-plane retardation value in a short wavelength is larger than an in-plane retardation value in a long wavelength, and the ¼ wavelength plate preferably satisfies the optical characteristics represented by formulae (50) and (51). Re(λ) represents an in-plane retardation value for light with a wavelength of λ nm. A circularly polarizing plate including the ¼ wavelength plate having the optical characteristics represented by formulae (50) and (51) tends to be excellent in antireflection characteristics since uniform polarized light conversion characteristics are obtained for lights each having a wavelength in a visible light region.

$$Re(450)/Re(550) \leq 1.00 \tag{50}$$

$$1.00 \leq Re(630)/Re(550) \tag{51}$$

The substrate may be a retardation film having a ½ wavelength plate function.

Examples of the resin constituting the substrate include polyolefins such as polyethylene, polypropylene, and norbornene-based polymer; a cycloolefin-based resin; polyvinyl alcohol; polyethylene terephthalate; a polymethacrylic acid ester; a polyacrylic acid ester; cellulose esters such as triacetyl cellulose, diacetyl cellulose, and cellulose acetate propionate; polyethylene naphthalate; polycarbonate; polysulfone; polyether sulfone; polyether ketone; polyphenylenesulfide; and polyphenylene oxide. The resin is preferably a cellulose ester, a cycloolefin-based resin, polycarbonate, polyethersulfone, polyethyleneterephthalate, or a polymethacrylic acid ester.

The cellulose ester is cellulose in which at least a part of hydroxyl groups contained in the cellulose is esterified, and the cellulose ester is commercially available. A substrate containing the cellulose ester is also commercially available. Examples of the commercially available substrate containing the cellulose ester include Fujitac (registered trademark) film (manufactured by FUJIFILM Corporation), KC8UX2M, KC8UY, and KC4UY (manufactured by Konica Minolta Opto Products Co., Ltd.).

The cycloolefin-based resin includes a cycloolefin polymer such as norbornene or a polycyclic norbornene-based monomer, and their copolymers. The cycloolefin-based resin may include a ring-opening structure, or may be obtained by hydrogenation of a cycloolefin-based resin including a ring-opening structure. Further, the cycloolefin-based resin may include a structural unit derived from a chain olefin and a vinylated aromatic compound to an extent that the transparency is not considerably deteriorated and that the hygroscopicity is not considerably increased. The cycloolefin-based resin may have a polar group introduced in its molecule.

Examples of the chain olefin include ethylene and propylene, and examples of the vinylated aromatic compound include styrene, α-methylstyrene, and alkyl-substituted styrene.

When the cycloolefin-based resin is a copolymer of a cycloolefin with a chain olefin or a vinylated aromatic compound, the content of a structural unit derived from the cycloolefin is usually not more than 50 mol %, and preferably 15 to 50 mol % to the entire structural units of the copolymer.

When the cycloolefin-based resin is a terpolymer of a cycloolefin, a chain olefin, and a vinylated aromatic compound, the content of a structural unit derived from the chain olefin is usually 5 to 80 mol % to the entire structural units of the copolymer; and the content of the structural unit derived from the vinylated aromatic compound is usually 5 to 80 mol % to the entire structural units of the copolymer. The terpolymer has an advantage that the use amount of a costly cycloolefin can be relatively reduced.

The cycloolefin-based resin is commercially available. Examples of the commercially available cycloolefin-based resin include Topas (registered trademark) (manufactured by Ticona), ARTON (registered trademark) (manufactured by JSR Corporation), ZEONOR (registered trademark) and ZEONEX (registered trademark) (both manufactured by Zeon Corporation), and APEL (registered trademark) (manufactured by Mitsui Chemicals, Inc.). Such a cycloolefin-based resin can be formed into a film by a conventional means such as a solvent casting method or a melt extrusion method to obtain a substrate. Examples of the substrate containing the commercially available cycloolefin-based resin include Escena (registered trademark) (manufactured by Sekisui Chemical Co., Ltd), SCA40 (registered trademark) (manufactured by Sekisui Chemical Co., Ltd), ZEONOR film (registered trademark) (manufactured by Optes Co., Ltd.), and ARTON film (registered trademark) (manufactured by JSR Corporation).

The substrate may be subjected to surface treatment. Examples of the surface treatment method include a method of treating a substrate surface with corona or plasma under vacuum to atmospheric pressure; a method of treating a substrate surface with laser; a method of treating a substrate surface with ozone; a method of saponifying a substrate surface; a method of treating a substrate surface with flame; a method of applying a coupling agent to a substrate surface; a method of treating a substrate surface with primer; and a graft polymerization method of allowing a reactive monomer or a polymer having reactivity to adhere to a substrate surface, and then reacting the monomer or polymer by irradiation with radiation, plasma or ultraviolet. Among them, a method of treating a substrate surface with corona or plasma under vacuum to atmospheric pressure is preferable.

Examples of the method of treating a substrate surface with corona or plasma include a method in which a substrate is arranged between mutually opposite electrodes, corona or plasma is generated under near-atmospheric pressure, thereby treating the surface of the substrate; a method in which a gas is led between mutually opposite electrodes, plasma of the gas is generated between the electrodes, and the gas in a plasma state is sprayed to the substrate; and a method in which glow electric discharge plasma is generated in a low pressure condition, thereby treating the surface of the substrate.

Among them, preferred is a method in which a substrate is arranged between mutually opposite electrodes, corona or plasma is generated under near-atmospheric pressure, thereby treating the surface of the substrate; or a method in which a gas is led between mutually opposite electrodes, plasma of the gas is generated between the electrodes, and the gas in a plasma state is sprayed to the substrate. Such a surface treatment by corona or plasma is usually performed by a commercially available surface treatment device.

The substrate may have a protective film on a surface reverse to the surface onto which the present composition is applied. Examples of the protective film include polyethylene, polyethylene terephthalate, polycarbonate, and polyolefin films, as well as films having an adhesive layer on these films. Among them, a polyethylene terephthalate film is preferable since having slight thermal deformation at the time of drying. When the substrate has a protective film on a surface reverse to the surface onto which the present composition is applied, shaking of the film and slight vibration of the coated surface in conveying the substrate can be suppressed, and uniformity of a coating can be improved.

The thickness of the substrate is preferable as it is thinner in terms of the weight adequate for practical handling, but if it is too thin, the strength tends to be low and the processability tends to be inferior. The thickness of the substrate is usually 5 to 300 µm, and preferably 20 to 200 µm.

The length of the substrate in the longitudinal direction is usually 10 to 3000 m, and preferably 100 to 2000 m. The length of the substrate in the short direction is usually 0.1 to 5 m, and preferably 0.2 to 2 m.

<Orientation Film>

The orientation film in the present invention has an orientation controlling force for orientating a polymerizable liquid crystal compound in a desired direction.

The orientation film preferably has solvent resistance not to be dissolved by application of the present composition, and also has heat resistance to stand a heat treatment for removing a solvent or orientating a polymerizable liquid crystal compound. Examples of the orientation film include an orientation film containing an orientational polymer, a photo-orientation film, and a groove orientation film having irregular patterns or a plurality of grooves formed for orientation on the surface.

Examples of the orientational polymer include polyamide and gelatins having an amide bond in the molecule, polyimide having an imide bond in the molecule and a polyamic acid which is a hydrolyzed product of the polyimide, polyvinyl alcohol, alkyl-modified polyvinyl alcohol, polyacrylamide, polyoxazole, polyethyleneimine, polystyrene, polyvinyl pyrrolidone, polyacrylic acid, and a polyacrylic acid ester. Among them, polyvinyl alcohol is preferable. Two or more kinds of the orientational polymers may be used in combination.

The orientation film containing an orientational polymer is usually formed on a surface of a substrate by applying a composition containing an orientational polymer dissolved in a solvent (hereinafter, may also be referred to as an orientational polymer composition) to a substrate and removing the solvent, or by applying an orientational polymer composition to a substrate, removing the solvent, and rubbing the composition (rubbing method).

Examples of the solvent include water; alcohol solvents such as methanol, ethanol, ethylene glycol, isopropyl alcohol, propylene glycol, methyl cellosolve, butyl cellosolve, and propylene glycol monomethyl ether; ester solvents such as ethyl acetate, butyl acetate, ethylene glycol methyl ether acetate, γ-butyrolactone, propylene glycol methyl ether acetate, and ethyl lactate; ketone solvents such as acetone, methyl ethyl ketone, cyclopentanone, cyclohexanone, methyl amyl ketone, and methyl isobutyl ketone; aliphatic hydrocarbon solvents such as pentane, hexane, and heptane; aromatic hydrocarbon solvents such as toluene and xylene; nitrile solvents such as acetonitrile; ether solvents such as tetrahydrofuran and dimethoxyethane; and chlorinated hydrocarbon solvents such as chloroform and chlorobenzene. These solvents may be used alone, or two or more kinds of them may be used in combination.

The concentration of the orientational polymer in the orientational polymer composition should be within a range in which an orientational polymer material can be completely dissolved in a solvent, and it is preferably 0.1 to 20% by mass and more preferably about 0.1 to 10% by mass in terms of the solid content with respect to the solution.

As the orientational polymer composition, a commercially available orientation film material may be used as it is. Examples of the commercially available orientation film material include SUNEVER (registered trademark, manufactured by Nissan Chemical Industries, Ltd.) and OPTOMER (registered trademark, manufactured by JSR Corporation).

Examples of the method of applying the orientational polymer composition to the substrate includes known methods such as coating methods including a spin coating method, an extrusion method, a gravure coating method, a die coating method, a slit coating method, a bar coating method, and an applicator method, and printing methods such as a flexo method. When the present polarizing film is produced by a continuous production method of Roll-to-Roll mode described later, a gravure coating method, a die coating method, or a printing method such as a flexo method is usually adopted in the application method.

Examples of the method of removing the solvent contained in the orientational polymer composition include a natural drying method, a ventilation drying method, heat drying, and a reduced-pressure drying method.

To provide the orientation film with an orientation controlling force, rubbing can be conducted (rubbing method) if necessary. The direction of the orientation controlling force can be controlled arbitrarily by selecting the direction for rubbing.

Examples of the method of providing the orientation controlling force by the rubbing method include a method for bringing a film of the orientational polymer, which is formed on the substrate surface by applying the orientational polymer composition to the substrate and annealing the orientational polymer composition, into contact with a rotating rubbing roll on which a rubbing cloth is wound.

The photo-orientation film is usually formed on a surface of a substrate by applying a composition containing a photo-reactive group-containing polymer or monomer and a solvent (hereinafter, may also be referred to as a "composition for forming a photo-orientation film") to a substrate, and irradiating the composition with light (preferably, polarized UV). The photo-orientation film is more preferable in that the direction of the orientation controlling force can be arbitrarily controlled by selecting the polarization direction of light to be irradiated.

The photo-reactive group refers to a group which generates liquid crystal orientating ability by light irradiation. Specifically, examples of the photo-reactive group include groups involved in orientation induction of molecules generated by light irradiation, or in photoreaction which originates the liquid crystal orientating ability, such as isomerization reaction, dimerization reaction, photo-crosslinking reaction, or photo-degradation reaction. Among them, a photo-reactive group involved in dimerization reaction or photo-crosslinking reaction is preferable because it is excellent in orientation. The photo-reactive group preferably has an unsaturated bond, particularly a double bond, and particularly preferably at least one bond selected from the group consisting of a carbon-carbon double bond (C=C bond), a carbon-nitrogen double bond (C=N bond), a nitrogen-nitrogen double bond (N=N bond), and a carbon-oxygen double bond (C=O bond).

Examples of the photo-reactive group having a C=C bond include a vinyl group, a polyene group, a stilbene group, a stilbazole group, a stilbazolium group, a chalcone group, and a cinnamoyl group. Examples of the photo-reactive group having a C=N bond include groups having a structure of an aromatic Schiff base, an aromatic hydrazone, etc. Examples of the photo-reactive group having a N=N bond include an azobenzene group, an azonaphthalene group, an aromatic heterocyclic azo group, a bisazo group, a formazan group, and a group having a structure of azoxybenzene. Examples of the photo-reactive group having a C=O bond include a benzophenone group, a coumarin group, an anthraquinone group, and a maleimide group. These groups may have a substituent group such as an alkyl group, an alkoxy group, an aryl group, an allyloxy group, a cyano group, an alkoxycarbonyl group, a hydroxyl group, a sulfonic acid group, or a halogenated alkyl group.

Among them, a photo-reactive group involved in photo-dimerization reaction is preferable, and a cinnamonyl group and a chalcone group are preferable in that the polarized light irradiation dose necessary for photo-orientation is relatively low and a photo-orientation film excellent in heat stability and stability with lapse of time is easily obtained. The photo-reactive group-containing polymer particularly preferably has a cinnamonyl group so that a cinnamic acid structure is formed at a terminal portion of the polymer side chain.

Examples of the solvent contained in the composition for forming a photo-orientation film include the same solvents as those contained in the foregoing orientational polymer composition, and the solvent may be selected appropriately depending on the solubility of the photo-reactive group-containing polymer or monomer.

The content of the photo-reactive group-containing polymer or monomer in the composition for forming a photo-orientation film can be appropriately adjusted depending on the kind of the polymer or monomer and the thickness of an objective photo-orientation film; however, it is preferably at least 0.2% by mass and more preferably in a range of 0.3 to 10% by mass. The composition for forming a photo-orientation film may contain a polymer material such as polyvinyl alcohol or polyimide and a photosensitizer to an extent that the characteristics of the photo-orientation film are not significantly deteriorated.

Examples of the method of applying the composition for forming a photo-orientation film to the substrate include the same method as that of applying the orientational polymer composition to the substrate. Examples of the method of removing the solvent from the composition for forming a photo-orientation film to be applied include the same method as that of removing the solvent from the orientational polymer composition.

The manner of polarized light irradiation may be a manner of directly irradiating the composition for forming a photo-orientation film, from which the solvent has been removed, applied onto a base board with polarized UV, or a manner of irradiating a substrate side with polarized light, thereby transmitting the polarized light. In particular, the polarized light is preferably substantially parallel light. The wavelength of the polarized light for irradiation preferably falls within a wavelength region in which the photo-reactive group of the photo-reactive group-containing polymer or monomer can easily absorb light energy. Specifically, UV (ultraviolet rays) falling within a wavelength range of 250 to 400 nm is particularly preferable. Examples of the light source to be used for the polarized light irradiation include a xenon lamp, a high pressure mercury lamp, a super-high pressure mercury lamp, a metal halide lamp, ultraviolet laser of KrF or ArF, etc., and a high pressure mercury lamp, super-high pressure mercury lamp, and a metal halide lamp are more preferable. These lamps are preferable since having high emission intensity of ultraviolet rays with a wavelength of 313 nm. Light from the light source may be radiated through a proper polarizer to carry out polarized UV irradiation. As such a polarizer, a polarizing filter, polarizing prisms of Glan-Thomson and Glan-Taylor, and a wire-grid type polarizer are usable.

When rubbing or polarized light irradiation is carried out with masking, a plurality of regions (patterns) having different liquid crystal orientation directions (patterns) can also be formed.

The groove orientation film is a film in which liquid crystal orientation is obtained by irregular patterns or a plurality of grooves on a surface of the film. H. V. Kennel et al. report the fact that when liquid crystal molecules are placed on a substrate having a plurality of linear grooves arranged at regular intervals, liquid crystal molecules are orientated to a direction along the grooves (Physical Review A24 (5), p. 2713, 1981).

Specific examples for forming a groove orientation film on a surface of a substrate include a method in which the surface of a photo-sensitive polyimide film is exposed via an exposure mask having periodically patterned slits, then, development and rinse treatment are conducted to remove an unnecessary polyimide film, thereby forming irregular patterns; a method in which a UV curable resin layer is formed on a plate-shaped master having grooves on its surface, and the resin layer is transferred onto a substrate film before curing; and a method in which a substrate film having a UV curable resin layer formed thereon is conveyed, and a roll-shaped master having a plurality of grooves is pressed against a surface of the UV curable resin layer to form irregularities before curing. The methods described in JP-A-H06-34976 and JP-A-2011-242743 can be used.

Of the above-described methods, a method in which a roll-shaped master having a plurality of grooves is pressed against a surface of the UV curable resin layer to form irregularities before curing is preferable. As the roll-shaped master, stainless (SUS) steel can be used from the viewpoint of durability.

As the UV curable resin, a polymer of a monofunctional acrylate, a polymer of a polyfunctional acrylate, or a polymer of a mixture of them can be used.

The monofunctional acrylate is a compound having in the molecule one group selected from the group consisting of an acryloyloxy group (CH2=CH—COO—) and a methacryloyloxy group (CH2=C(CH3)-COO—) (hereinafter, may also be referred to as a (meth)acryloyloxy group).

Examples of the monofunctional acrylate having one (meth)acryloyloxy group include alkyl (meth)acrylates having 4 to 16 carbon atoms, β-carboxyalkyl (meth)acrylates having 2 to 14 carbon atoms, alkylated phenyl (meth) acrylates having 2 to 14 carbon atoms, methoxypolyethylene glycol (meth)acrylate, phenoxy polyethylene glycol (meth) acrylate, and isobornyl (meth)acrylate.

The polyfunctional acrylate is usually a compound having in the molecule two to six (meth)acryloyloxy groups.

Examples of the bifunctional acrylate having two (meth) acryloyloxy groups include 1,3-butanediol di(meth)acrylate; 1,6-hexanediol di(meth)acrylate; ethylene glycol di(meth) acrylate; diethylene glycol di(meth)acrylate; neopentyl glycol di(meth)acrylate; triethylene glycol di(meth)acrylate; tetraethylene glycol di(meth)acrylate; polyethylene glycol diacrylate; bis(acryloyloxyethyl) ether of bisphenol A; ethoxylated bisphenol A di(meth)acrylate; propoxylated neopentyl glycol di(meth)acrylate; ethoxylated neopentyl glycol di(meth)acrylate; and 3-methylpentanediol di(meth) acrylate.

Examples of the polyfunctional acrylate having three to six (meth)acryloyloxy groups include trimethylolpropane tri(meth)acrylate; pentaerythritol tri(meth)acrylate; tris(2-hydroxyethyl) isocyanurate tri(meth)acrylate; ethoxylated trimethylolpropane tri(meth)acrylate; propoxylated trimethylolpropane tri(meth)acrylate; pentaerythritol tetra(meth) acrylate; dipentaerythritol penta(meth)acrylate; dipentaerythritol hexa(meth)acrylate; tripentaerythritol tetra (meth)acrylate; tripentaerythritol penta(meth)acrylate; tripentaerythritol hexa(meth)acrylate; tripentaerythritol hepta(meth)acrylate; tripentaerythritol octa(meth)acrylate;

a reaction product of pentaerythritol tri(meth)acrylate with an acid anhydride; a reaction product of dipentaerythritol penta(meth)acrylate with an acid anhydride;
a reaction product of tripentaerythritol hepta(meth)acrylate with an acid anhydride;
caprolactone-modified trimethylolpropane tri(meth)acrylate; caprolactone-modified pentaerythritol tri(meth)acrylate; caprolactone-modified tris(2-hydroxyethyl) isocyanurate tri(meth)acrylate; caprolactone-modified pentaerythritol tetra(meth)acrylate; caprolactone-modified dipentaerythritol penta(meth)acrylate; caprolactone-modified dipentaerythritol hexa(meth)acrylate; caprolactone-modified tripentaerythritol tetra(meth)acrylate; caprolactone-modified tripentaerythritol penta(meth)acrylate; caprolactone-modified tripentaerythritol hexa(meth)acrylate; caprolactone-modified tripentaerythritol hepta(meth)acrylate; caprolactone-modified tripentaerythritol octa(meth)acrylate; a reaction product of caprolactone-modified pentaerythritol tri(meth) acrylate with an acid anhydride; a reaction product of caprolactone-modified dipentaerythritol penta(meth)acrylate with an acid anhydride; and a reaction product of caprolactone-modified tripentaerythritol hepta(meth)acrylate with an acid anhydride. In specific examples of the polyfunctional acrylate listed above, the (meth)acrylate denotes acrylate or methacrylate. The caprolactone-modified means that a ring-opening body of caprolactone or a ring-opening polymer of caprolactone is introduced between an alcohol-derived portion and a (meth)acryloyloxy group of a (meth)acrylate compound.

As the poly-functional acrylate, commercially available products can also be used.

Examples of the commercially available product include A-DOD-N, A-HD-N, A-NOD-N, APG-100, APG-200, APG-400, A-GLY-9E, A-GLY-20E, A-TMM-3, A-TMPT, AD-TMP, ATM-35E, A-TMMT, A-9550, A-DPH, HD-N, NOD-N, NPG, TMPT (manufactured by Shin Nakamura Chemical Co., Ltd.); "ARONIX M-220", "ARONIX M-325", "ARONIX M-240", "ARONIX M-270", "ARONIX M-309", "ARONIX M-310", "ARONIX M-321", "ARONIX M-350", "ARONIX M-360", "ARONIX M-305", "ARONIX M-306", "ARONIX M-450", "ARONIX M-451", "ARONIX M-408", "ARONIX M-400", "ARONIX M-402", "ARONIX M-403", "ARONIX M-404", "ARONIX M-405", "ARONIX M-406" (manufactured by Toagosei Co., Ltd.), "EBECRYL 11", "EBECRYL 145", "EBECRYL 150", "EBECRYL 40", "EBECRYL 140", "EBECRYL 180", DPGDA, HDDA, TPGDA, HPNDA, PETIA, PETRA, TMPTA, TMPEOTA, DPHA, and EBECRYL series (manufactured by Daicel-Cytec Company, Ltd.).

In the irregularities of the groove orientation film, the width of a convex portion is preferably 0.05 to 5 μm, the width of a concave portion is preferably 0.1 to 5 μm, and the depth of the difference in the irregularity is not more than 2 μm, preferably 0.01 to not more than 1 μm. When the difference falls within this range, liquid crystal orientation having small orientation disorder can be obtained.

The thickness of the orientation film is usually in a range of 10 nm to 10000 nm, preferably in a range of 10 nm to 1000 nm, and more preferably in a range of 10 nm to 500 nm.

Examples of the method of applying the present composition include the same method as the method of applying the orientational polymer composition to the substrate.

<Step (B)>

When the present composition contains a solvent, usually, the solvent is removed from the formed coating film. Examples of the method of removing the solvent include a natural drying method, a ventilation drying method, heat drying, and a reduced-pressure drying method.

The polymerizable liquid crystal compound contained in the formed coating film is usually heated to not less than a temperature for transition to a solution state, and then cooled to a temperature for liquid crystal orientation to form an orientated liquid crystal phase.

The temperature for orientating the polymerizable liquid crystal compound contained in the formed coating film should be determined by previously observing the texture using a composition containing the polymerizable liquid crystal compound. The solvent removal and the liquid crystal orientation may be carried out simultaneously. The temperature at that time is preferably in a range of 50 to 200° C. although depending on the kind of the solvent to be removed and the kind of the polymerizable liquid crystal compound, and more preferably in a range of 80 to 130° C. when the substrate is a resin substrate.

When a circularly polarizing plate having the present polarizing film and a ¼ wavelength plate is obtained using a substrate which is the ¼ wavelength plate, the orientation direction of the polymerizable liquid crystal compound may be determined such that an angle between the transmission axis of the polarizing film to be obtained and the slow axis (optical axis) of the substrate is substantially 45°.

<Step (C)>

The orientated polymerizable liquid crystal compound is irradiated with an active energy ray to polymerize the polymerizable liquid crystal compound.

When the orientated polymerizable liquid crystal compound is polymerized, a polarizing film containing the polymerizable liquid crystal compound polymerized in an orientated state and compound (1) orientated together with the polymerizable liquid crystal compound is obtained.

A polarizing film containing a polymerizable liquid crystal compound polymerized with retaining a smectic liquid crystal phase has high polarizing performance as compared with a conventional host-guest type polarizing film, i.e., a polarizing film obtained by polymerizing a polymerizable liquid crystal compound or the like with retaining a nematic liquid crystal phase, and is also excellent in polarizing performance and strength as compared with a polarizing film obtained by applying only a dichroic dye or a liquid crystal compound of the lyotropic liquid crystal type.

A light source for the active energy ray should be one which can emit ultraviolet ray, electron beam, x-ray, etc., and is preferably a light source having a light emission distribution in a wavelength of not more than 400 nm, such as a low pressure mercury lamp, a medium pressure mercury lamp, a high pressure mercury lamp, a super-high pressure mercury lamp, a chemical lamp, a black light lamp, a microwave excitation mercury lamp, or a metal halide lamp.

The irradiation energy of the active energy ray is set such that a wavelength region effective to activate the polymerization initiator preferably has a radiation intensity of 10 to 5000 mJ/cm$^2$, and more preferably 100 to 2000 mJ/cm$^2$. If the irradiation energy is lower than 10 mJ/cm$^2$, curing of the polymerizable liquid crystal compound tends to be insufficient.

The thickness of the present polarizing film thus formed is preferably not less than 0.5 μm and not more than 10 μm, more preferably not less than 1 μm and not more than 5 μm. The thickness of the present polarizing film can be determined by measurement with an interference thickness meter, a laser microscope, or a contact-type thickness meter.

The present polarizing film particularly preferably exhibits a Bragg peak in x-ray diffractometry. Examples of the present polarizing film exhibiting a Bragg peak include those exhibiting a diffraction peak derived from a hexatic phase or a crystal phase.

A maximum absorption ($\lambda_{max1}$) of the present polarizing film is preferably present in a range of 350 to 550 nm, more preferably present in a range of 410 to 540 nm, and still more preferably present in a range of 430 to 530 nm. $\lambda_{max1}$ preferably shifts to longer wavelength as compared with a maximum absorption ($\lambda_{max2}$) measured by dissolving compound (1), which is contained in the present polarizing film, in a suitable solvent. Such shift to longer wavelength is developed when compound (1) is dispersed between molecule chains formed by a polymerized polymerizable liquid crystal compound, and shows that compound (1) strongly interacts with the molecular chain. The shift to longer wavelength means that a difference between absorption maximums ($\lambda_{max1}-\lambda_{max2}$) becomes a positive value, and the difference is preferably not less than 15 nm and more preferably not less than 30 nm.

The dichroic ratio of the present polarizing film is preferably not less than 15 and more preferably not less than 25.

When the substrate used is not a ¼ wavelength plate, a circularly polarizing plate can be obtained by stacking the resulting present polarizing film and a ¼ wavelength plate. In this case, it is preferable to perform stacking such that an angle between the transmission axis of the present polarizing film and the slow axis (optical axis) of the ¼ wavelength plate is substantially 45°. When the transmission axis of the present polarizing film and the optical axis of a retardation film such as a ¼ wavelength plate are aligned or are orthogonal to each other, a polarizing plate functioning as an optical compensation film can also be obtained.

The present polarizing film and the ¼ wavelength plate may be stacked together with a substrate having the present polarizing film formed thereon or a substrate having an orientation film formed thereon, or may be stacked while removing the substrate or both the substrate and the orientation film. The present polarizing film, formed on a surface of the substrate or a surface of the substrate having an orientation film formed thereon, and the ¼ wavelength plate can be stacked by sticking the surface on which the present polarizing film is formed and the ¼ wavelength plate with an adhesive and then removing the substrate or the substrate having an orientation film formed thereon. In this case, the adhesive may be applied to the present polarizing film or the ¼ wavelength plate.

<Continuous Production Process for Present Polarizing Film>

The present polarizing film is preferably continuously produced in a Roll-to-Roll manner. One example of a main part of a continuous production process for the present polarizing film in a Roll-to-Roll manner will be described with reference to FIG. 1.

A first roll 210, in which a substrate is wound up on a first winding core 210A, is easily available, for example, from the market. Examples of the substrate in the form of a roll and available from the market include, among the substrates listed above, films made of a cellulose ester, a cyclic olefin-based resin, a polycarbonate, polyethylene terephthalate, and a polymethacrylic acid ester.

Successively, the substrate is wound off from the first roll 210. The substrate is wound off by arranging a suitable rotary means at the winding core 210A of the first roll 210 and rotating the first roll 210 by the rotary means. Alternatively, a suitable auxiliary roll 300 may be arranged in a conveyance direction of the substrate from the first roll 210 in order to wind off the substrate by a rotary means of an auxiliary roll 300. Furthermore, by arranging a rotary means together with the first winding core 210A and the auxiliary roll 300, the substrate may be wound off while providing the substrate with a suitable tension.

On a surface of the substrate wound off from the first roll 210, a composition for forming a photo-orientation film is applied by means of an application device 211A, when the substrate passes through the application device 211A. As the application device 211A for continuously applying the composition for forming a photo-orientation film, preferred is a gravure coating method, a die coating method or a flexo method.

The substrate which has passed through the application device 211A is conveyed to a drying furnace 212A, and dried in the drying furnace 212A to continuously form a first coating film on the surface of the substrate. For example, hot air type drying furnace, in which a ventilation drying method and a heat drying method are combined, is used as the drying furnace 212A. The preset temperature of the drying furnace 212A is determined depending on the kind of a solvent contained in the composition for forming a photo-orientation film. The drying furnace 212A may comprise multiple zones having different preset temperatures, or may comprise multiple drying furnaces having different preset temperatures and arranged in series.

A photo-orientation film is obtained by irradiating the resulting first coating film with polarized light by means of a polarized UV irradiation device 213A.

Successively, the substrate, on which the photo-orientation film has been formed, passes through an application device 211B. After the present composition containing the solvent is applied on the photo-orientation film by means of the application device 211B. Then, a second coating film, in which the polymerizable liquid crystal compound contained in the present composition is orientated, is obtained by passing through a drying furnace 212B. The drying furnace 212B serves to remove the solvent from the present composition containing the solvent, which is applied on the photo-orientation film, and simultaneously serves to provide thermal energy in order to orientate the polymerizable liquid crystal compound contained in the composition. As is the case in the drying furnace 212A, the drying furnace 212B may comprise multiple zones having different preset temperatures, or comprise multiple drying furnaces having different preset temperatures and arranged in series.

The substrate is conveyed to an active energy ray irradiation device 213B in such a state that the polymerizable liquid crystal compound contained in the second coating film is orientated. In the active energy ray irradiation device 213B, active energy rays are irradiated. By active energy ray irradiation with the active energy ray irradiation device 213B, the polymerizable liquid crystal compound is polymerized in the orientated state to obtain a polarizing film.

Thus, the continuously produced present polarizing plate produced in a continuous manner is wound up on a second winding core 220A to obtain a second roll 220. In winding it up, it may also be wound up together with a suitable spacer.

Thus, the substrate passes from the first roll 210 through the application device 211A, the drying furnace 212A, the polarized UV irradiation device 213A, the application device 211B, the drying furnace 212B, and the active energy ray irradiation device 213B in order, and as a result, the present polarizing plate can be continuously produced in a Roll-to-Roll manner.

The production process shown in FIG. 1 represents a process for continuously producing the present polarizing film. For example, a substrate passes from a first roll through the application device 211A, the drying furnace 212A and the polarized UV irradiation device 213A in order, and is wound up on a winding core to produce a roll-shaped laminated product of the substrate and a photo-orientation film. Furthermore, the roll-shaped laminated product is wound off, and passed through the application device 211B, the drying furnace 212B, and the active energy ray irradiation device 213B in order, and as a result, the present polarizing film can be continuously produced.

When the present polarizing film is produced in the form of the second roll 220, the present polarizing film in a long form may be wound off from the second roll 220 and cut into a prescribed size, and then, a ¼ wavelength plate may be stuck to the cut polarizing film to produce a circularly polarizing plate. Additionally, a circular polarizing plate in a long form may also be continuously produced by setting a third roll in which a ¼ wavelength plate in a long form is wound up on a winding core.

Figure 2:
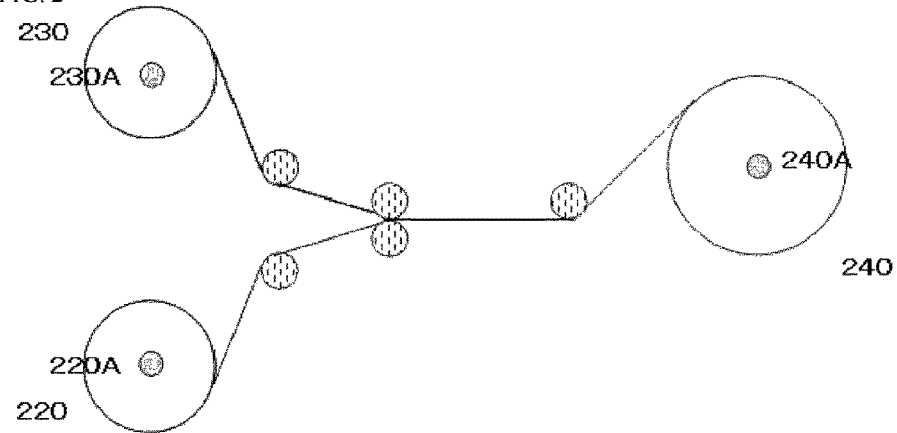
FIG. 2 is a schematic diagram of a process for continuously producing a circularly polarizing plate having the present polarizing film.

A process for continuously producing a circularly polarizing plate in a long form will be described with reference to FIG. 2. The production process includes the steps of:

continuously winding off the present polarizing film from the second roll 220 while continuously winding off a ¼ wavelength plate in a long form from a third roll 230 in which the ¼ wavelength plate in a long form is wound up;

continuously sticking the present polarizing film to the ¼ wavelength plate in a long form to obtain a circular polarizing plate in a long form; and winding up the resulting circular polarizing plate in a long form on a fourth winding core 240A to obtain a fourth roll 240. This process is so-called Roll-to-Roll sticking. An adhesive agent may be used in sticking.

<Use of Present Polarizing Film>

The present polarizing film and the circularly polarizing plate having the present polarizing film and the ¼ wavelength plate can be used for various kinds of display devices.

The display device refers to a device comprising a display element, that is, a device comprising a luminescent element or luminescent device as a luminescent source. Examples of the display device comprising the present polarizing film include a liquid crystal display device, an organic electroluminescence (EL) display device, an inorganic electroluminescence (EL) display device, an electron emission display device (such as a field emission display device (FED) and surface-conduction electron-emitter display (SED)), an electronic paper (a display device with an electronic ink or an electrophoresis element, a plasma display device, a projection type-display device (such as a grating light valve (GLV) display device, a display device comprising a digital micromirror device (DMD)) and a piezoceramic display. The liquid crystal display device may be a transmissive liquid crystal display, a semi-transmissive liquid crystal display, a reflective liquid crystal display, a direct viewing liquid crystal display or a projection liquid crystal display. These display devices may also be display devices displaying a two-dimensional image or stereoscopic display devices displaying a three-dimensional image.

The present polarizing film can be particularly effectively used for a liquid crystal display device, an organic electroluminescence (EL) display device, and an inorganic electroluminescence (EL) display device.

The circularly polarizing plate having the present polarizing film and the ¼ wavelength plate can be particularly effectively used for an organic electroluminescence (EL) display device and an inorganic electroluminescence (EL) display device.

When the present polarizing film is used for a liquid crystal display device, the present polarizing film may be provided outside or inside a liquid crystal cell.

Figure 3:
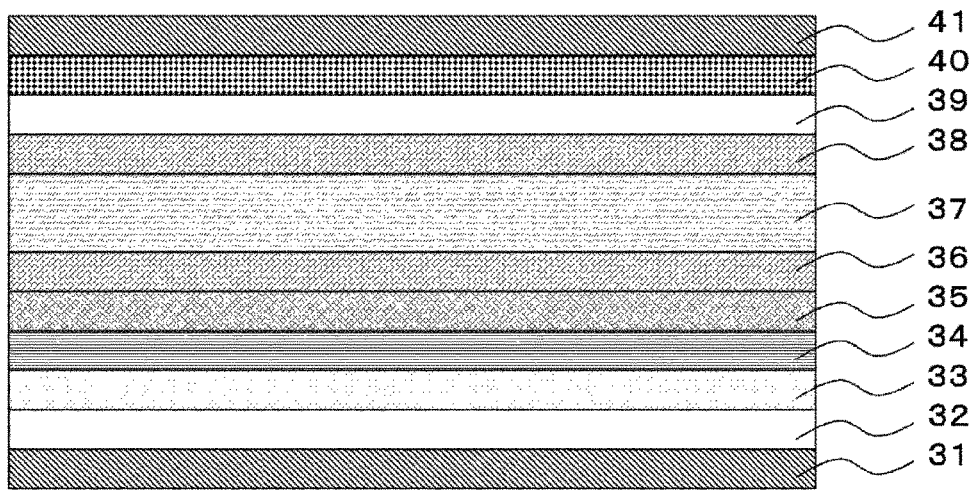
FIG. 3 is a schematic diagram of a liquid crystal cell including the present polarizing film.

In particular, a first configuration in the case where the present polarizing film is provided inside a liquid crystal cell of a transmissive color liquid crystal display device of active matrix type will be hereinafter described with reference to FIG. 3. A display device 30 is constituted of a first base 31, a first polarizing film 32 of the present invention, a color filter layer 33, a planarizing layer 34, an ITO electrode layer 35, a first orientation film 36, a liquid crystal layer 37, a second orientation film 38, a second polarizing film 39 of the present invention, a TFT layer 40 including thin-film transistor circuit and pixel electrodes, and a second base 41.

The color filter layer denotes a layer in which light having a desired wavelength is taken out from incident light from the base 41 side and, for example, may be a layer which absorbs light having a wavelength other than a desired wavelength from white light and allows only the light having a desired wavelength to pass therethrough, or a layer which allows wavelength conversion of a wavelength of incident light to emit light having a desired wavelength.

The present first and second polarizing films may each include the orientation film on the first and second base sides. The orientation film may be a rubbing orientation film, or may be a photo-orientation film.

The present first polarizing film may include a retardation layer.

Figure 4:
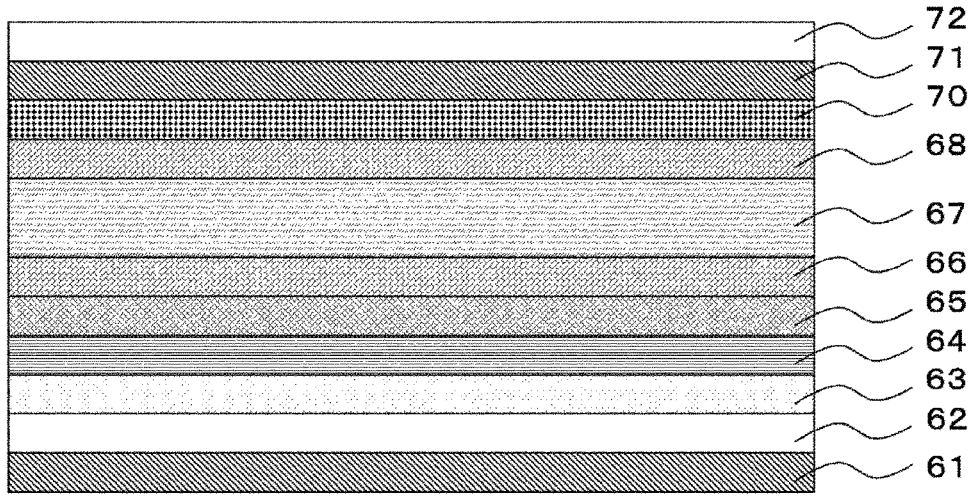
FIG. 4 is a schematic diagram of a liquid crystal cell including the present polarizing film.

Next, a second configuration will be hereinafter described with reference to FIG. 4. A display device 60 is constituted of a first base 61, a first polarizing film 62 of the present invention, a color filter layer 63, a planarizing layer 64, an ITO electrode layer 65, a first orientation film 66, a liquid crystal layer 67, a second orientation film 68, a TFT layer 70 including thin-film transistor circuit and pixel electrodes, a second base 71, and a second polarizing film 72.

The second polarizing film 72 located on the opposite side of the TFT layer 70 of the second base 71 may be the present polarizing film or a polarizing film produced by dyeing a polyvinyl alcohol film with iodine and then stretching the polyvinyl alcohol film.

Figure 5:
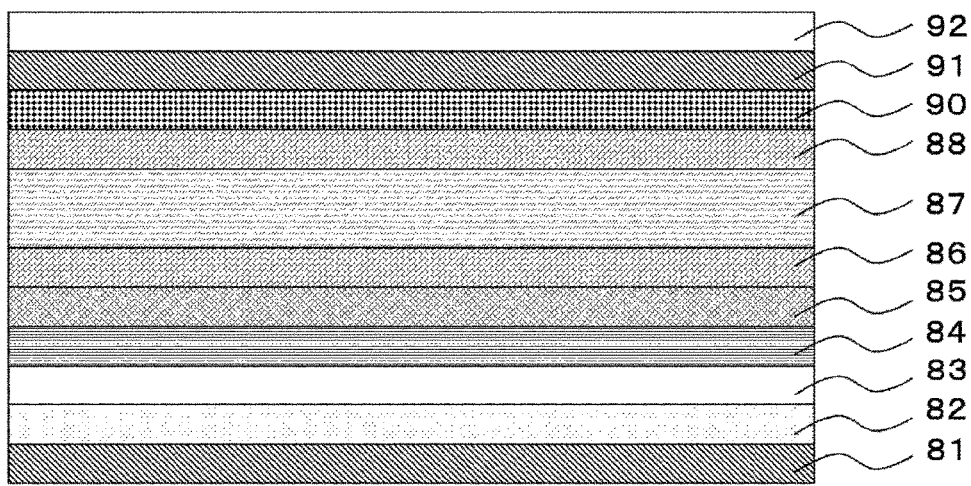
FIG. 5 is a schematic diagram of a liquid crystal cell including the present polarizing film.

A third configuration will be hereinafter described with reference to FIG. 5. A display device 80 is constituted of a first base 81, a color filter layer 82, a first polarizing film 83 of the present invention, a planarizing layer 84, an ITO electrode layer 85, a first orientation film 86, a liquid crystal layer 87, a second orientation film 88, a TFT layer 90 including thin-film transistor circuitry and pixel electrodes, a second base 91, and a second polarizing film 92.

In the third configuration, the second polarizing film 92 may be the present polarizing film or a polarizing film produced by dyeing a polyvinyl alcohol film with iodine and then stretching the polyvinyl alcohol film. When the second polarizing film 92 is the present polarizing film, the second polarizing film may be located between the second base 91 and the TFT layer 90 as in the case of the first configuration.

The color filter layer 82 in the third configuration may be located on the opposite side of a liquid crystal layer of the first substrata 81.

Polarized light is scattered by particles included in the color filter layer, so that depolarization may occur. Thus, among the first to third configurations, the third configuration is more preferable because the first polarizing film according to the present invention is located on the liquid crystal layer side relative to the color filter layer.

EXAMPLES

Hereinafter, the present invention will be described in more detail by examples. "%" and "part(s)" in the examples refer to % by mass and part(s) by mass, unless otherwise described.

Example 1

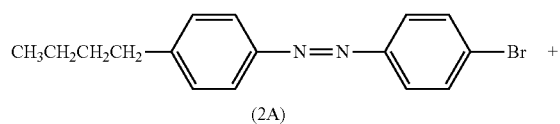

(2A)

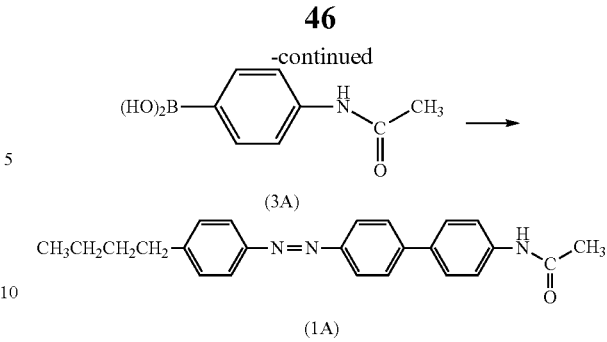

A compound represented by formula (2A) (0.15 g), a compound represented by formula (3A) (0.10 g), potassium phosphate (0.50 g), tris(dibenzylideneacetone)dipalladium (0) (0.0087 g), tri-tert-butylphosphonium tetrafluoroborate (0.011 g), and 1,4-dioxane (3 g) were mixed. The resulting mixture was stirred at 100° C. for 18 hours under a nitrogen atmosphere. The resulting reaction mixture was condensed and then purified by silica gel column chromatography (eluate: chloroform). The resulting solid was washed with acetonitrile and then dried, thus obtaining 0.03 g of a compound which is represented by formula (1A) and is an orange solid (hereinafter referred to as compound (1A)).

Mw: 371 (GC-MS)

Maximum absorption wavelength ($\lambda_{max2}$)=360 nm (Chloroform solution)

Example 2

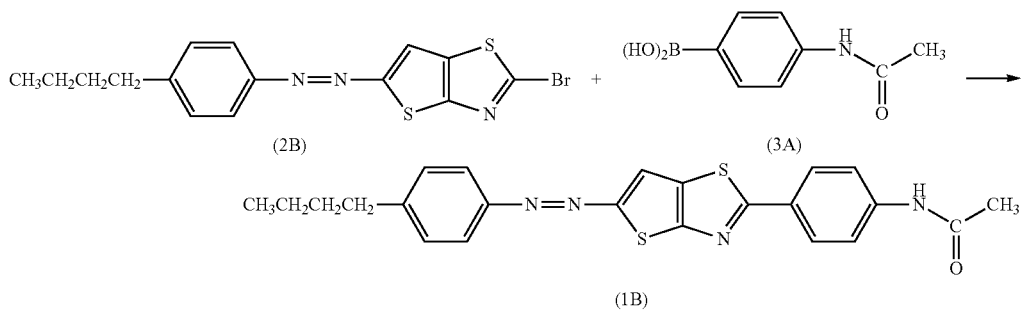

A compound represented by formula (2B) (0.30 g), a compound represented by formula (3A) (0.21 g), potassium acetate (0.38 g), [1,1'-bis(diphenylphosphino)ferrocene]dichloropalladium (II) (0.129 g), and diethylene glycol dimethyl ether (18.0 g) were mixed. The resulting mixture was stirred at 140° C. for 3 hours under a nitrogen atmosphere. The resulting reaction mixture was condensed and then purified by silica gel column chromatography (eluate: chloroform). The resulting solid was washed with acetonitrile and then dried, thus obtaining 0.010 g of a compound which is represented by formula (1B) and is an orange solid (hereinafter referred to as compound (1B)).

Mw: 434 (LC-MS)

Maximum absorption wavelength ($\lambda_{max2}$)=437 nm (Chloroform solution)

Example 3

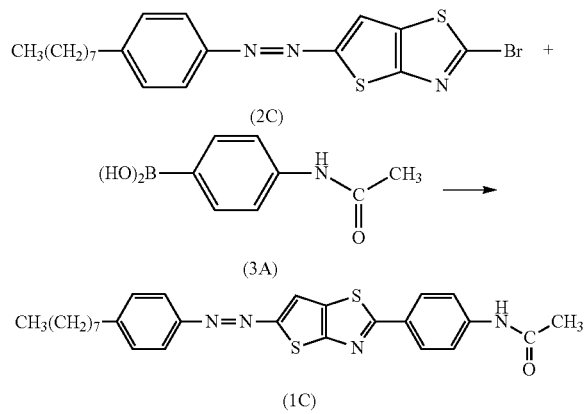

A compound represented by formula (2C) (0.40 g), a compound represented by formula (3A) (0.25 g), potassium acetate (0.45 g), [1,1'-bis(diphenylphosphino)ferrocene]dichloropalladium(II) (0.150 g), and diethylene glycol dimethyl ether (24.0 g) were mixed. The resulting mixture was stirred at 140° C. for 3 hours under a nitrogen atmosphere. The resulting reaction mixture was condensed and then purified by silica gel column chromatography (eluate: chloroform). The resulting solid was washed with acetonitrile and then dried, thus obtaining 0.032 g of a compound which is represented by formula (1C) and is an orange solid (hereinafter referred to as compound (1C)).

Mw: 490 (LC-MS)

Maximum absorption wavelength ($\lambda_{max2}$)=438 nm (Chloroform solution)

[Polymerizable Liquid Crystal Compound]

A compound represented by the following formula (4-6) (hereinafter referred to as compound (4-6)), a compound represented by the following formula (4-8) (hereinafter referred to as compound (4-8)), a compound represented by the following formula (4-14) (hereinafter referred to as compound (4-14)), and a compound represented by the following formula (4-17) (hereinafter referred to as compound (4-17)) were used.

Compound (4-6) was synthesized by the method described in Lub et al. Recl. Trav. Chim. Pays-Bas, 115, 321-328 (1996). Compound (4-8) was produced in accordance with this method.

Compounds (4-14) and (4-17) were produced in accordance with the method described in Japanese Patent No. 4719156.

Compound (4-6):

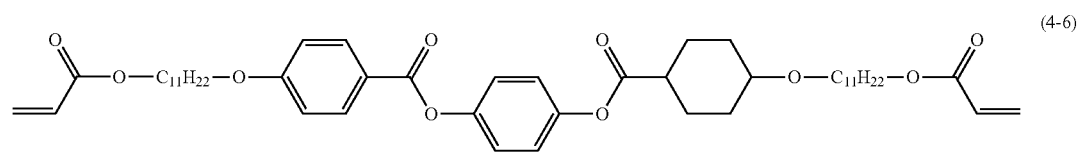

[Measurement of Phase Transition Temperature]

The phase transition temperature of compound (4-6) was confirmed by determining the phase transition temperature of a film formed of compound (4-6). The operation is as follows.

A film formed of compound (4-6) was formed on a glass base board having an orientation film formed thereon, and a phase transition temperature was confirmed by texture observation with a polarizing microscope (BX-51, manufactured by Olympus Corporation), while performing heating. After the temperature of compound (4-6) increased to 120° C., when the temperature decreased, the compound caused phase transition to a nematic phase at 112° C., to a smectic A phase at 110° C., and to a smectic B phase at 94° C.

Compound (4-8):

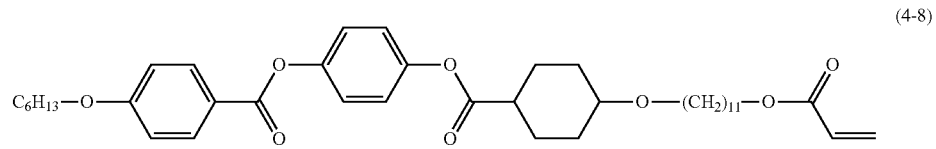

[Measurement of Phase Transition Temperature]

The phase transition temperature of compound (4-8) was confirmed in the same manner as in measurement of the phase transition temperature of compound (4-6). After the temperature of compound (4-8) increased to 140° C., when the temperature decreased, the compound caused phase transition to a nematic phase at 131° C., to a smectic A phase at 80° C., and to a smectic B phase at 68° C.

Compound (4-14):

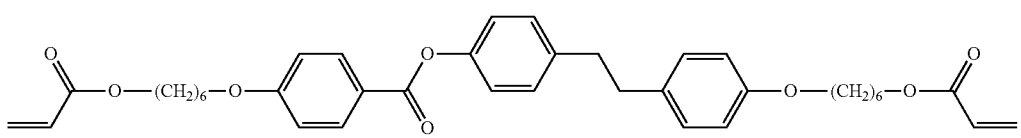

(4-14)

[Measurement of Phase Transition Temperature]

The phase transition temperature of compound (4-14) was confirmed in the same manner as in measurement of the phase transition temperature of compound (4-6). After the temperature of compound (4-14) increased to 140° C., when the temperature decreased, the compound caused phase transition to a nematic phase at 106° C., to a smectic A phase at 103° C., and to a smectic B phase at 86° C.

Compound (4-17):

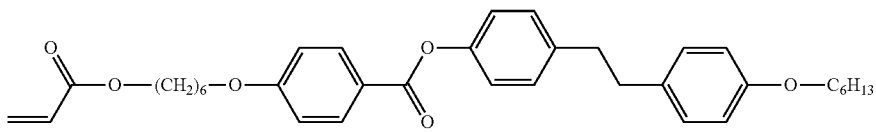

(4-17)

[Measurement of Phase Transition Temperature]

The phase transition temperature of compound (4-17) was confirmed in the same manner as in measurement of the phase transition temperature of compound (4-6). After the temperature of compound (4-17) increased to 140° C., when the temperature decreased, the compound caused phase transition to a nematic phase at 119° C., to a smectic A phase at 100° C., and to a smectic B phase at 77° C.

Example 4

[Preparation of Composition]

The following components were mixed and then stirred at 80° C. for 1 hour, thus obtaining composition (1).

Polymerizable liquid crystal compound:

| compound (4-6) | 75 parts |
| compound (4-8) | 25 parts |

Compound (1):

| compound (1A) | 2.5 parts |

Polymerization Initiator:

| 2-dimethylamino-2-benzyl-1-(4-morpholinophenyl)butane-1-one (Irgacure 369; manufactured by Ciba Specialty Chemicals) | 6 parts |

Leveling Agent:

| polyacrylate compound (BYK-361N; manufactured by BYK-Chemie) | 1.5 parts |

Solvent:

| chloroform | 250 parts |

[Measurement of Phase Transition Temperature]

As in the case of compound (4-6), the phase transition temperature of the component contained in composition (1) was obtained. After the temperature of such a component increased to 140° C., when the temperature decreased, the component caused phase transition to a nematic phase at 115° C., to a smectic A phase at 105° C., and to a smectic B phase at 75° C.

[Production of Polarizing Film and its Evaluation]

1. Formation of Orientation Film

An aqueous solution of 2 mass % polyvinyl alcohol (Polyvinyl Alcohol 1000 perfectly saponified type, manufactured by Wako Pure Chemical Industries, Ltd.) was applied onto a glass base board by a spin coating method and then dried. Then, a film having a thickness of 100 nm was formed. Subsequently, a surface of the resulting film was subjected to rubbing treatment, thus forming an orientation film. The rubbing treatment was carried out by a semi-automatic rubbing device (product name: LQ-008 type, manufactured by Joyo Engineering Co., Ltd.) with the use of cloth (product name: YA-20-RW, manufactured by Yoshikawa Chemical Co., Ltd.) under conditions of a pushing amount of 0.15 mm, a rotation speed of 500 rpm, and 16.7 mm/s. Laminate 1 having an orientation film formed on the glass base board was obtained by the rubbing treatment.

2. Formation of Polarizing Film

Composition (1) was applied onto the orientation film of laminate 1 by a spin coating method, dried by heating on a hot plate at 120° C. for 1 minute, and then rapidly cooled to room temperature, thus forming a dry film containing a polymerizable liquid crystal compound orientated on the orientation film. Then, the dry film was irradiated with ultraviolet rays in an exposure amount of 2000 mJ/cm$^2$ (standard 365 nm) using a UV irradiation apparatus (SPOT CURE SP-7; manufactured by Ushio Inc.), so that the polymerizable liquid crystal compound contained in the dry film was polymerized with retaining an orientation state, thereby forming polarizing film (1) from the dry film and obtaining laminate 2. In this case, when the thickness of the polarizing film was measured by a laser microscope (OLS3000, manufactured by Olympus Corporation), it was 1.7 μm.

3. X-ray Diffractometry

Polarizing film (1) was subjected to X-ray diffractometry using an X-ray diffractometer X'Pert PRO MPD (manufactured by Spectris Co., Ltd.). X-rays generated by using Cu as a target under conditions of a X-ray tube current of 40 mA and X-ray tube voltage of 45 kV were made to enter from a rubbing direction (a rubbing direction of the orientation film provided under the polarizing film was previously obtained) through a fixed divergence slit ½°, and measurement was performed by scanning at a step: 2θ=0.01671° in a scanning range of 2θ=4.0 to 40.0°, so that a sharp diffraction peak (Bragg peak) in which a full width at half maximum (FWHM) of a peak was about 0.31° was obtained near 2θ=20.1°. An equivalent result was obtained also in the case of incidence from a rubbing vertical direction. An order cycle (d) obtained from the peak position was about 4.4 Å, and it was found that a structure exhibiting a higher order smectic phase was formed.

4. Measurement of Dichroic Ratio

Absorbance (A$^1$) in the transmission axis direction and absorbance (A$^2$) in the absorption axis direction in a maximum absorption wavelength were measured by a double beam method using a device in which a folder provided with laminate 2 was set in a spectrophotometer (UV-3150, manufactured by Shimadzu Corporation). In the folder, a mesh for cutting a light amount by 50% is installed on a reference side. Based on absorbance (A$^1$) in the transmission axis direction and absorbance (A$^2$) in the absorption axis direction thus measured, a ratio (A$^2$/A$^1$) was calculated and was used as a dichroic ratio. The maximum absorption wavelength ($\lambda_{max1}$) was 376 nm, and the dichroic ratio at this wavelength showed a value as high as 38. It can be said that a polarizing film having a higher dichroic ratio is more useful. Since the maximum absorption wavelength ($\lambda_{max2}$) of compound (1A) was 360 nm, it was found to be shifted to longer wavelength. The result of the shift to longer wavelength shows that when compound (1A) is dispersed between dense molecular chains formed by polymerization of the polymerizable liquid crystal compound in the present polarizing film, compound (1A) strongly interacts with the molecular chains.

A protective film (40 μm TAC ("KC4UY" manufactured by Konica Minolta, Inc.) is disposed on a surface of the formed polarizing film (1), and light is irradiated from the upper side under the following conditions, whereby light resistance is evaluated. The formed polarizing film is excellent in light resistance.

The light irradiation conditions in the light resistance test are as follows.

Equipment used: Suntest XLS+ manufactured by Atlas Material Testing Solutions
Light source used: xenon arc lamp
Exposure condition: 250 mW/m$^2$
Test time: 120 hours
Exposure dose: 108000 KJ/m$^2$
Temperature: 60° C.

Example 5

A composition and a polarizing film that contain compound (1B) are obtained in the same manner as in Example 4, except that compound (1B) is used instead of compound (1A) in Example 4.

Example 6

A composition and a polarizing film that contain compound (1C) are obtained in the same manner as in Example 4, except that compound (1C) is used instead of compound (1A) in Example 4.

Example 7

A compound represented by formula (1D) is obtained in the same manner as in Example 1, except that a compound represented by formula (2D) is used instead of the compound represented by formula (2A) in Example 1.

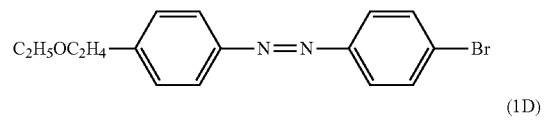

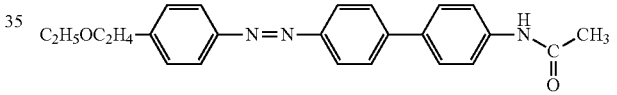

Example 8

A composition and a polarizing film that contain compound (1D) are obtained in the same manner as in Example 4, except that compound (1D) is used instead of compound (1A) in Example 4.

Example 9

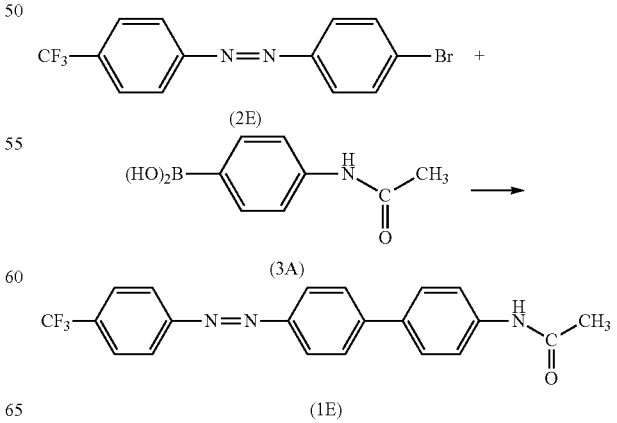

A compound represented by formula (2E) (0.30 g), a compound represented by formula (3A) (0.25 g), potassium acetate (0.45 g), [1,1'-bis(diphenylphosphino)ferrocene]dichloropalladium(II) (0.15 g), and diethylene glycol dimethyl ether (18 g) were mixed. The resulting mixture was stirred at 140° C. for 3 hours under a nitrogen atmosphere. The resulting reaction mixture was condensed and then purified by silica gel column chromatography (eluate: tetrahydrofuran). The resulting solid was washed with acetonitrile and then dried, thus obtaining 0.14 g of a compound which is represented by formula (1E) and is an orange solid (hereinafter referred to as compound (1E)). The yield based on compound (2E) was 40%.

M/Z: 384 (EI-MS)

Maximum absorption wavelength ($\lambda_{max2}$)=363 nm (Chloroform solution)

$^1$H-NMR (DMSO-d6): δ (ppm) 2.06 (s, 3H), 7.73 (m, 4H), 7.95 (m, 4H), 8.03 (m, 4H), 10.1 (s, 1H).

Example 10

A polarizing film was produced in the same manner as in Example 4, except that compound (1E) was used instead of compound (1A). When the maximum absorption wavelength and the dichroic ratio were measured similarly, the maximum absorption wavelength ($\lambda_{max1}$) was 392 nm, and the dichroic ratio showed a value as high as 30. As described in Example 9, since the maximum absorption wavelength ($\lambda_{max2}$) was 363 nm, it was found to be shifted to longer wavelength. This result shows that when compound (1E) is dispersed between dense molecular chains formed by polymerization of the polymerizable liquid crystal compound in the polarizing film, compound (1E) strongly interacts with the molecular chains.

Example 11

A compound represented by formula (1F) is obtained in the same manner as in Example 1, except that a compound represented by formula (2F) is used instead of the compound represented by formula (2A) in Example 1.

(2F)

(1F)

Example 12

A composition and a polarizing film that contain compound (1F) are obtained in the same manner as in Example 4, except that compound (1F) is used instead of compound (1A) in Example 4.

Example 13

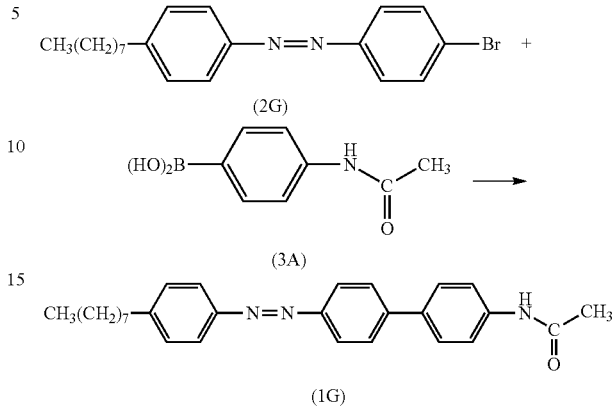

A compound represented by formula (2G) (0.30 g), a compound represented by formula (3A) (0.22 g), potassium acetate (0.39 g), [1,1'-bis(diphenylphosphino)ferrocene]dichloropalladium(II) (0.13 g), and diethylene glycol dimethyl ether (18 g) were mixed. The resulting mixture was stirred at 140° C. for 3 hours under a nitrogen atmosphere. The resulting reaction mixture was condensed and then purified by silica gel column chromatography (eluate: tetrahydrofuran). The resulting solid was washed with acetonitrile and then dried, thus obtaining 0.26 g of a compound which is represented by formula (1G) and is an orange solid (hereinafter referred to as compound (1G)). The yield based on compound (2G) was 76%.

M/Z: 428 (EI-MS)

Maximum absorption wavelength ($\lambda_{max2}$)=360 nm (Chloroform solution)

$^1$H-NMR (CDCl$_3$): δ (ppm) 0.88 (t, 3H), 1.30 (m, 10H), 1.63 (t, 2H), 2.21 (s, 3H), 2.68 (t, 2H), 7.25 (d, 2H), 7.33 (d, 2H), 7.67 (m, 4H), 7.85 (d, 2H), 7.96 (d, 2H).

Example 14

A polarizing film was produced in the same manner as in Example 4, except that compound (1G) was used instead of compound (1A). When the maximum absorption wavelength and the dichroic ratio were measured similarly, the maximum absorption wavelength ($\lambda_{max1}$) was 380 nm, and the dichroic ratio showed a value as high as 60. As described in Example 13, since the maximum absorption wavelength ($\lambda_{max2}$) was 360 nm, it was found to be shifted to longer wavelength. This result shows that when compound (1G) is dispersed between dense molecular chains formed by polymerization of the polymerizable liquid crystal compound in the polarizing film, compound (1G) strongly interacts with the molecular chains.

Example 15

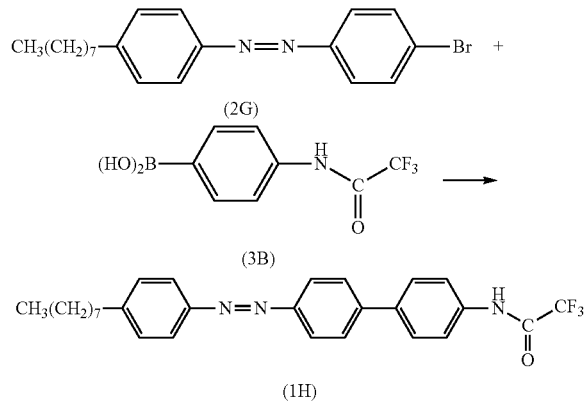

A compound represented by formula (2G) (0.30 g), a compound represented by formula (3B) (0.30 g), potassium phosphate (0.85 g), tris(dibenzylideneacetone)dipalladium (0) (0.0147 g), tri-tert-butylphosphonium tetrafluoroborate (0.0187 g), and 1,4-dioxane (6 g) were mixed. The resulting mixture was stirred at 100° C. for 5 hours under a nitrogen atmosphere. The resulting reaction mixture was condensed and then purified by silica gel column chromatography (eluate: tetrahydrofuran). The resulting solid was washed with acetonitrile and then dried, thus obtaining 0.11 g of a compound which is represented by formula (1H) and is an orange solid (hereinafter referred to as compound (1H)). The yield based on compound (2G) was 28%.

M/Z: 482 (EI-MS)

Maximum absorption wavelength ($\lambda_{max2}$)=355 nm (Chloroform solution)

INDUSTRIAL APPLICABILITY

The novel compound of the present invention is a compound having a maximum absorption in a wavelength range of 350 nm to 550 nm and functioning as a dichroic dye, and the composition of this invention containing the compound provides a polarizing film having a high dichroic ratio.

DESCRIPTION OF SYMBOLS

210 First roll
210A Winding core
220 Second roll
220A Winding core
211A, 211B Application device
212A, 212B Drying furnace
213A Polarized UV irradiation device
213B Active energy ray irradiation device
300 Auxiliary roll
230 Third roll
230A Winding core
240 Fourth roll
240A Winding core
300 Auxiliary roll

The invention claimed is:

1. A composition comprising a polymerizable liquid crystal compound and a compound represented by formula (1):

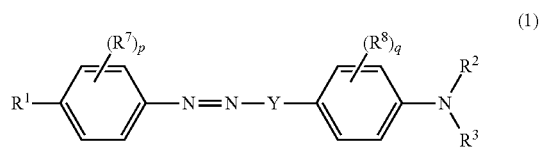

wherein $R^1$ represents an alkyl group having 1 to 20 carbon atoms, an alkoxy group having 1 to 20 carbon atoms, an acyl group having 1 to 20 carbon atoms, an alkoxycarbonyl group having 2 to 20 carbon atoms, an acyloxy group having 1 to 20 carbon atoms, or —N($R^{10}$)($R^{11}$), wherein $R^{10}$ represents an acyl group having 1 to 20 carbon atoms, an alkylsulfonyl group having 1 to 20 carbon atoms, or an arylsulfonyl group having 6 to 20 carbon atoms, $R^{11}$ represents a hydrogen atom or an alkyl group having 1 to 20 carbon atoms, $R^{10}$ and $R^{11}$ are optionally joined together to form a ring containing —N—CO— or —N—SO$_2$— together with the nitrogen atom to which they are bonded, at least one hydrogen atom constituting the alkyl group, the alkoxy group, the acyl group, the alkoxycarbonyl group, the acyloxy group, the alkylsulfonyl group, and the arylsulfonyl group is optionally replaced by a halogen atom, a hydroxy group, an amino group, or an amino group having a substituent, and —O— or —NR$^{20}$— is optionally inserted between carbon atoms constituting the alkyl group and the alkoxy group, wherein $R^{20}$ represents a hydrogen atom or an alkyl group having 1 to 20 carbon atoms;

$R^7$ and $R^8$ are substituents other than a hydrogen atom, each independently represents an alkyl group having 1 to 4 carbon atoms, an alkoxy group having 1 to 4 carbon atoms, a halogen atom, or a cyano group, at least one hydrogen atom constituting the alkyl group having 1 to 4 carbon atoms and the alkoxy group having 1 to 4 carbon atoms is optionally substituted with a halogen atom or a hydroxy group, p and q are each independently an integer from 0 to 2;

$R^2$ represents an acyl group having 1 to 20 carbon atoms, an alkylsulfonyl group having 1 to 20 carbon atoms, or an arylsulfonyl group having 6 to 20 carbon atoms; $R^3$ represents a hydrogen atom or an alkyl group having 1 to 20 carbon atoms, $R^2$ and $R^3$ are optionally joined together to form a ring containing —N—CO— or —N—SO$_2$— together with the nitrogen atom to which they are bonded, at least one hydrogen atom constituting the acyl group, the alkylsulfonyl group, and the arylsulfonyl group is optionally replaced by a halogen atom, a hydroxy group, an amino group, or an amino group having a substituent, and —O— or —NR$^{21}$— is optionally inserted between carbon atoms constituting the alkyl group and the alkoxy group, wherein $R^{21}$ represents a hydrogen atom or an alkyl group having 1 to 20 carbon atoms; and Y represents a group of formula (Y1):

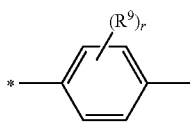
(Y1)

wherein * represents a bonding site with N; $R^9$ is a substituent other than a hydrogen atom, and independently represents an alkyl group having 1 to 4 carbon atoms, an alkoxy group having 1 to 4 carbon atoms, a halogen atom, or a cyano group, at least one hydrogen atom constituting the alkyl group having 1 to 4 carbon atoms and the alkoxy group having 1 to 4 carbon atoms is optionally substituted with a halogen atom or a hydroxy group; r is an integer from 0 to 2,
or a group of formula (Y2):

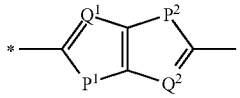
(Y2)

wherein * represents a bonding site with N; $P^1$ and $P^2$ each independently represent —S—, —O—, or —N($R^{12}$)—, wherein $R^{12}$ represents a hydrogen atom or an alkyl group having 1 to 4 carbon atoms; and $Q^1$ and $Q^2$ each independently represent =N— or =CH—.

2. The composition according to claim 1, wherein p, q, and r are 0.

3. The composition according to claim 1, wherein the polymerizable liquid crystal compound exhibits a smectic liquid crystal phase.

4. The composition according to claim 1, further comprising a polymerization initiator.

5. A polarizing film comprising a compound represented by formula (1):

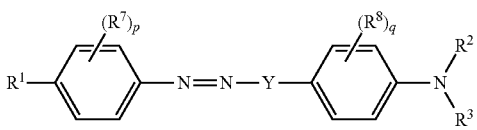
(1)

wherein $R^1$ represents an alkyl group having 1 to 20 carbon atoms, an alkoxy group having 1 to 20 carbon atoms, an acyl group having 1 to 20 carbon atoms, an alkoxycarbonyl group having 2 to 20 carbon atoms, an acyloxy group having 1 to 20 carbon atoms, or —N($R^{10}$)($R^{11}$), wherein $R^{10}$ represents an acyl group having 1 to 20 carbon atoms, an alkylsulfonyl group having 1 to 20 carbon atoms, or an arylsulfonyl group having 6 to 20 carbon atoms, $R^{11}$ represents a hydrogen atom or an alkyl group having 1 to 20 carbon atoms, $R^{10}$ and $R^{11}$ are optionally joined together to form a ring containing —N—CO— or —N—SO$_2$— together with the nitrogen atom to which they are bonded, at least one hydrogen atom constituting the alkyl group, the alkoxy group, the acyl group, the alkoxycarbonyl group, the acyloxy group, the alkylsulfonyl group, and the arylsulfonyl group is optionally replaced by a halogen atom, a hydroxy group, an amino group, or an amino group having a substituent, and —O— or —NR$^{20}$— is optionally inserted between carbon atoms constituting the alkyl group and the alkoxy group, wherein $R^{20}$ represents a hydrogen atom or an alkyl group having 1 to 20 carbon atoms;

$R^7$ and $R^8$ are substituents other than a hydrogen atom, each independently represents an alkyl group having 1 to 4 carbon atoms, an alkoxy group having 1 to 4 carbon atoms, a halogen atom, or a cyano group, at least one hydrogen atom constituting the alkyl group having 1 to 4 carbon atoms and the alkoxy group having 1 to 4 carbon atoms is optionally substituted with a halogen atom or a hydroxy group, p and q are each independently an integer from 0 to 2;

$R^2$ represents an acyl group having 1 to 20 carbon atoms, an alkylsulfonyl group having 1 to 20 carbon atoms, or an arylsulfonyl group having 6 to 20 carbon atoms; $R^3$ represents a hydrogen atom or an alkyl group having 1 to 20 carbon atoms, $R^2$ and $R^3$ are optionally joined together to form a ring containing —N—CO— or —N—SO$_2$— together with the nitrogen atom to which they are bonded, at least one hydrogen atom constituting the acyl group, the alkylsulfonyl group, and the arylsulfonyl group is optionally replaced by a halogen atom, a hydroxy group, an amino group, or an amino group having a substituent, and —O— or —NR$^{21}$— is optionally inserted between carbon atoms constituting the alkyl group and the alkoxy group, wherein $R^{21}$ represents a hydrogen atom or an alkyl group having 1 to 20 carbon atoms; and Y represents a group of formula (Y1):

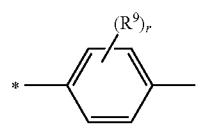
(Y1)

wherein * represents a bonding site with N; $R^9$ is a substituent other than a hydrogen atom, and independently represents an alkyl group having 1 to 4 carbon atoms, an alkoxy group having 1 to 4 carbon atoms, a halogen atom, or a cyano group, at least one hydrogen atom constituting the alkyl group having 1 to 4 carbon atoms and the alkoxy group having 1 to 4 carbon atoms is optionally substituted with a halogen atom or a hydroxy group; r is an integer from 0 to 2,
or a group of formula (Y2):

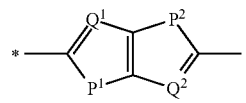
(Y2)

wherein * represents a bonding site with N; $P^1$ and $P^2$ each independently represent —S—, —O—, or —N($R^{12}$)—, wherein $R^{12}$ represents a hydrogen atom or an alkyl group having 1 to 4 carbon atoms; and $Q^1$ and $Q^2$ each independently represent =N— or =CH—.

6. A polarizing film formed of the composition according to claim 1.

7. The polarizing film according to claim 5, wherein a maximum absorption wavelength ($\lambda_{max1}$) of the polarizing film is longer than a maximum absorption wavelength ($\lambda_{max2}$) of the compound represented by formula (1).

8. The polarizing film according to claim 7, wherein a difference between $\lambda_{max1}$ and $\lambda_{max2}$ is not less than 15 nm.

9. The polarizing film according to claim 5, wherein a Bragg peak is exhibited in X-ray diffractometry.

10. A liquid crystal display device comprising the polarizing film according to claim 5.

11. A liquid crystal cell comprising the polarizing film according to claim 5, a liquid crystal layer, and a base.

12. The liquid crystal cell according to claim 11, wherein the polarizing film is disposed between the base and the liquid crystal layer.

13. The liquid crystal cell according to claim 12, wherein a color filter is further disposed between the base and the liquid crystal layer.

14. A circularly polarizing plate comprising the polarizing film according to claim 5 and a ¼ wavelength plate.

15. An organic EL display device comprising the polarizing film according to claim 5 and an organic EL element.

16. An organic EL display device comprising the circularly polarizing plate according to claim 14 and an organic EL element.

* * * * *